(12) United States Patent
Messerschmidt et al.

(10) Patent No.: US 11,060,967 B2
(45) Date of Patent: Jul. 13, 2021

(54) METHOD AND APPARATUS FOR DETERMINING MARKERS OF HEALTH BY ANALYSIS OF BLOOD

(71) Applicant: NUEON INC., San Francisco, CA (US)

(72) Inventors: Robert G. Messerschmidt, San Francisco, CA (US); Howland D. T. Jones, Rio Rancho, NM (US)

(73) Assignee: NUEON INC., Menlo Park, CA (US)

( * ) Notice: Subject to any disclaimer, the term of this patent is extended or adjusted under 35 U.S.C. 154(b) by 679 days.

(21) Appl. No.: 15/620,269

(22) Filed: Jun. 12, 2017

(65) Prior Publication Data

US 2017/0350814 A1 Dec. 7, 2017

Related U.S. Application Data

(63) Continuation of application No. 14/634,238, filed on Feb. 27, 2015, now abandoned.
(Continued)

(51) Int. Cl.
*A61B 5/00* (2006.01)
*G01N 21/25* (2006.01)
(Continued)

(52) U.S. Cl.
CPC ........... *G01N 21/27* (2013.01); *A61B 5/0075* (2013.01); *A61B 5/02* (2013.01); *A61B 5/4833* (2013.01);
(Continued)

(58) Field of Classification Search
None
See application file for complete search history.

(56) References Cited

U.S. PATENT DOCUMENTS

| 4,514,050 A | 4/1985 | Stites |
| 4,775,637 A | 10/1988 | Sutherland et al. |

(Continued)

FOREIGN PATENT DOCUMENTS

| EP | 0476192 | 3/1992 |
| EP | 2700933 | 2/2014 |

(Continued)

OTHER PUBLICATIONS

Eigenvector Research Incorporated website. Accessed Apr. 30, 2015. http://www.eigenvector.com/software/solo.htm.
(Continued)

*Primary Examiner* — Neil N Turk
(74) *Attorney, Agent, or Firm* — FisherBroyles LLP; John Shimmick

(57) ABSTRACT

Biomarkers of high blood pressure are measured to identify high blood pressure of the subject based on one or more biomarkers. In many embodiments, the response of the biomarker to blood pressure occurs over the course of at least an hour, such that the high blood pressure identification is based on a cumulative effect of physiology of the subject over a period of time. The methods and apparatus of identifying high blood pressure with biomarkers have the advantage of providing improved treatment of the subject, as the identified biomarker can be related to an effect of the high blood pressure on the subject, such as a biomarker corresponding to central blood pressure. The sample can be subjected to increases in one or more of pressure or temperatures, and changes in the blood sample measured over time.

22 Claims, 26 Drawing Sheets

Related U.S. Application Data

(60) Provisional application No. 62/083,720, filed on Nov. 24, 2014, provisional application No. 62/005,522, filed on May 30, 2014, provisional application No. 61/984,244, filed on Apr. 25, 2014, provisional application No. 61/946,494, filed on Feb. 28, 2014.

(51) Int. Cl.
  G01N 21/59 (2006.01)
  G01N 21/27 (2006.01)
  G01N 33/49 (2006.01)
  A61B 5/02 (2006.01)
  A61B 5/15 (2006.01)

(52) U.S. Cl.
  CPC .......... G01N 21/59 (2013.01); G01N 33/492 (2013.01); *G01N 2201/068* (2013.01); *G01N 2201/06113* (2013.01)

(56) References Cited

U.S. PATENT DOCUMENTS

| | | | |
|---|---|---|---|
| 4,882,492 A | 11/1989 | Schlager | |
| 5,139,328 A * | 8/1992 | Baker | G01N 15/05 356/39 |
| 5,200,609 A | 4/1993 | Sting | |
| 5,280,786 A | 1/1994 | Wlodarczyk | |
| 5,288,646 A | 2/1994 | Lundsgaard | |
| 5,327,777 A | 7/1994 | Kaye | |
| 5,331,958 A | 7/1994 | Oppenheimer | |
| 5,362,445 A | 11/1994 | Miyahara | |
| 5,366,903 A | 11/1994 | Lundsgaard | |
| 5,372,135 A * | 12/1994 | Mendelson | A61B 5/14532 356/39 |
| 5,437,840 A | 8/1995 | King et al. | |
| 5,525,518 A | 6/1996 | Lundsgaard | |
| 5,599,959 A | 2/1997 | Hosmane | |
| 5,636,640 A | 6/1997 | Staehlin | |
| 5,689,333 A | 11/1997 | Batchelder | |
| 5,706,208 A | 1/1998 | Osten | |
| 5,729,333 A | 3/1998 | Osten | |
| 5,830,133 A | 11/1998 | Osten | |
| 6,006,119 A | 12/1999 | Soller | |
| 6,064,474 A * | 5/2000 | Lee | G01N 21/314 356/39 |
| 6,084,661 A * | 7/2000 | Mendelson | G01N 21/314 250/343 |
| 6,141,100 A | 10/2000 | Burka | |
| 6,266,139 B1 | 7/2001 | Mannhardt | |
| 6,285,448 B1 | 9/2001 | Kuenstner | |
| 6,353,471 B1 | 3/2002 | Samsoondar | |
| 6,383,179 B1 | 5/2002 | Neuberger | |
| 6,603,987 B2 | 8/2003 | Whitson | |
| 6,614,730 B1 | 9/2003 | Vo-Dinh | |
| 6,638,769 B2 | 10/2003 | Lilja | |
| 6,676,903 B2 | 1/2004 | Potyrailo | |
| 6,788,394 B1 | 9/2004 | Garcia-Rubio | |
| 6,791,674 B2 * | 9/2004 | Kawano | G01N 21/359 356/39 |
| 6,866,675 B2 | 3/2005 | Perez | |
| 6,944,487 B2 | 9/2005 | Maynard | |
| 7,001,344 B2 | 2/2006 | Freeman | |
| 7,004,928 B2 | 2/2006 | Aceti | |
| 7,061,593 B2 * | 6/2006 | Braig | A61B 5/01 356/39 |
| 7,150,755 B2 | 12/2006 | LeVaughn | |
| 7,271,912 B2 | 9/2007 | Sterling | |
| 7,282,105 B1 | 10/2007 | Plunkett | |
| 7,291,497 B2 | 11/2007 | Holmes | |
| 7,299,711 B1 | 11/2007 | Linker | |
| 7,319,894 B2 | 1/2008 | Higgins | |
| 7,426,407 B2 | 9/2008 | Higgins | |
| 7,570,357 B2 | 8/2009 | Tsenkova | |
| 7,593,108 B2 | 9/2009 | Sterling | |
| 7,656,523 B2 | 2/2010 | Sun | |
| 7,787,109 B2 | 8/2010 | Dosmann | |
| 7,869,009 B2 | 1/2011 | Dosmann | |
| 7,969,307 B2 | 6/2011 | Peeters | |
| 8,033,898 B2 | 10/2011 | McNaughton et al. | |
| 8,041,538 B2 | 10/2011 | Meyer | |
| 8,077,042 B2 | 12/2011 | Peeters | |
| 8,160,665 B2 | 4/2012 | Mischler | |
| 8,184,273 B2 | 5/2012 | Dosmann | |
| 8,206,650 B2 | 6/2012 | Samsoondar | |
| 8,303,518 B2 | 11/2012 | Aceti | |
| 8,483,789 B2 | 7/2013 | Higgins | |
| 8,690,798 B2 | 4/2014 | Douglas | |
| 8,808,202 B2 | 8/2014 | Brancazio | |
| 8,821,412 B2 | 9/2014 | Gonzalez-Zugasti | |
| 8,821,413 B2 | 9/2014 | Effenhauser | |
| 8,830,449 B1 | 9/2014 | Lamego | |
| 8,900,514 B2 | 12/2014 | Forsell | |
| 9,113,836 B2 | 8/2015 | Bernstein | |
| 9,133,024 B2 | 9/2015 | Phan | |
| 9,217,706 B2 | 12/2015 | Mucci | |
| 9,259,175 B2 | 2/2016 | Stafford | |
| 9,291,504 B2 | 3/2016 | Goldring | |
| 9,341,515 B2 | 5/2016 | Schulte | |
| 9,377,396 B2 | 6/2016 | Goldring et al. | |
| 9,470,673 B2 | 10/2016 | Samsoondar | |
| 9,470,699 B2 | 10/2016 | Peeters | |
| 9,603,562 B2 | 3/2017 | Aceti | |
| 10,337,984 B2 | 7/2019 | Messerschmidt | |
| 2002/0122168 A1 | 9/2002 | Grcia-Rubio | |
| 2002/0123677 A1 | 9/2002 | Miki | |
| 2002/0156380 A1 | 10/2002 | Feld | |
| 2003/0018282 A1 | 1/2003 | Effenhauser | |
| 2003/0059948 A1 | 3/2003 | Hildenbrand | |
| 2003/0083686 A1 | 5/2003 | Freeman | |
| 2003/0171696 A1 | 9/2003 | Dosmann | |
| 2003/0175160 A1 | 9/2003 | Archibald | |
| 2003/0189707 A1 | 10/2003 | Naya | |
| 2003/0227628 A1 | 12/2003 | Kreimer | |
| 2004/0186359 A1 | 9/2004 | Beaudoin et al. | |
| 2005/0208501 A1 | 9/2005 | Goldrick | |
| 2005/0244952 A1 | 11/2005 | Cohen | |
| 2006/0043301 A1 | 3/2006 | Mantele | |
| 2006/0057554 A1 | 3/2006 | Watling | |
| 2006/0057642 A1 | 3/2006 | Kiefer et al. | |
| 2006/0074282 A1 | 4/2006 | Ward | |
| 2006/0135861 A1 | 6/2006 | Lucassen | |
| 2006/0166302 A1 | 7/2006 | Clarke | |
| 2006/0228258 A1 * | 10/2006 | Samsoondar | G01N 21/03 422/82.05 |
| 2007/0076208 A1 | 4/2007 | Koo | |
| 2007/0116602 A1 * | 5/2007 | Lee | G01N 24/08 422/82.01 |
| 2007/0134738 A1 | 6/2007 | Wells | |
| 2007/0149944 A1 * | 6/2007 | Tashiro | A61B 5/1545 604/413 |
| 2007/0213636 A1 | 9/2007 | Kuriger | |
| 2008/0138793 A1 | 6/2008 | Lindberg | |
| 2008/0153171 A1 | 6/2008 | Liu et al. | |
| 2008/0218734 A1 | 9/2008 | Higashi | |
| 2008/0218736 A1 | 9/2008 | Shaw | |
| 2008/0300508 A1 | 12/2008 | Tomer | |
| 2010/0105098 A1 | 4/2010 | Frederiske | |
| 2010/0121163 A1 | 5/2010 | Vestel | |
| 2010/0129919 A1 | 5/2010 | Levin et al. | |
| 2010/0136549 A1 * | 6/2010 | Christiansen | G06T 7/44 435/6.1 |
| 2010/0142773 A1 | 6/2010 | Cha | |
| 2010/0196945 A1 | 8/2010 | Forsell | |
| 2010/0245803 A1 | 9/2010 | Samsoondar | |
| 2010/0256524 A1 | 10/2010 | Levinson | |
| 2010/0284004 A1 | 11/2010 | Reich | |
| 2011/0003707 A1 | 1/2011 | Goix et al. | |
| 2011/0020849 A1 | 1/2011 | Spence | |
| 2011/0105952 A1 | 5/2011 | Bernstein | |
| 2011/0111435 A1 | 5/2011 | Dobson et al. | |
| 2011/0144463 A1 | 6/2011 | Pesach | |
| 2011/0172508 A1 | 7/2011 | Chickering | |
| 2011/0196239 A1 | 8/2011 | Behrend | |

(56) References Cited

U.S. PATENT DOCUMENTS

| | | | |
|---|---|---|---|
| 2011/0223654 | A1 | 9/2011 | Holman |
| 2011/0278472 | A1 | 11/2011 | Atzier |
| 2011/0287948 | A1 | 11/2011 | Suresh |
| 2012/0016818 | A1 | 1/2012 | Hackett |
| 2012/0142559 | A1 | 6/2012 | Tuytten |
| 2012/0205727 | A1 | 8/2012 | Kanakasabapathy |
| 2012/0257199 | A1 | 10/2012 | Liu et al. |
| 2012/0261256 | A1 | 10/2012 | Chang |
| 2012/0271125 | A1 | 10/2012 | Bernstein |
| 2012/0274934 | A1 | 11/2012 | Messerschmidt |
| 2013/0114068 | A1* | 5/2013 | Lim ............... A61B 5/150221 356/39 |
| 2013/0143226 | A1 | 6/2013 | Hill |
| 2013/0338013 | A1 | 12/2013 | Zhong |
| 2014/0112568 | A1 | 4/2014 | Liu |
| 2014/0148669 | A1 | 5/2014 | Saban |
| 2014/0336534 | A1 | 11/2014 | Balligand |
| 2014/0336536 | A1 | 11/2014 | Brancazio |
| 2015/0055121 | A1 | 2/2015 | Forsell |
| 2015/0057530 | A1 | 2/2015 | Roggeveen |
| 2015/0087944 | A1 | 3/2015 | Levinson |
| 2015/0208985 | A1 | 7/2015 | Huang |
| 2015/0338338 | A1 | 11/2015 | Messerschmidt et al. |
| 2016/0025624 | A1 | 1/2016 | Mucci |
| 2016/0029937 | A1 | 2/2016 | Sia |
| 2016/0058354 | A1 | 3/2016 | Phan |
| 2016/0066828 | A1 | 3/2016 | Phan |
| 2016/0123869 | A1 | 5/2016 | Messerschmidt |
| 2016/0151569 | A1 | 6/2016 | Stafford |
| 2016/0302707 | A1 | 10/2016 | Pesach |
| 2017/0010154 | A1 | 1/2017 | Spudich |
| 2017/0127990 | A1 | 5/2017 | Levinson |
| 2018/0136193 | A1 | 5/2018 | Messerschmidt |

FOREIGN PATENT DOCUMENTS

| | | | |
|---|---|---|---|
| EP | 3282937 | A1 | 2/2018 |
| GB | 740181 | A | 11/1955 |
| JP | 2002131319 | | 5/2002 |
| WO | 1986000513 | | 1/1986 |
| WO | 02058556 | | 8/2002 |
| WO | 03055379 | A2 | 7/2003 |
| WO | 2005080946 | | 9/2005 |
| WO | 2009117416 | | 9/2009 |
| WO | 2011153271 | A1 | 12/2011 |
| WO | 2013058084 | | 4/2013 |
| WO | WO-2013134786 | A2 | 9/2013 |
| WO | 2013156806 | A2 | 10/2013 |
| WO | WO-2013155458 | A1 | 10/2013 |
| WO | 2013180652 | A1 | 12/2013 |
| WO | 2013186628 | | 12/2013 |
| WO | 2014191980 | | 12/2014 |
| WO | 2015009970 | A1 | 1/2015 |
| WO | 2015112919 | | 7/2015 |
| WO | 2015131151 | A2 | 9/2015 |
| WO | 2015166237 | A1 | 11/2015 |
| WO | 2015179288 | A1 | 11/2015 |
| WO | 2015179969 | | 12/2015 |
| WO | 2016086071 | A1 | 6/2016 |
| WO | 2016168090 | A1 | 10/2016 |
| WO | 2017165403 | A1 | 9/2017 |
| WO | 2018085699 | A1 | 5/2018 |

OTHER PUBLICATIONS

International search report with written opinion dated Jul. 24, 2015 for PCT/US2015/018181.

Office action dated Jan. 8, 2016 for U.S. Appl. No. 14/634,238.

Office Action dated Dec. 19, 2016 for U.S. Appl. No. 14/634,238.

"International Search Report and Written Opinion dated Nov. 7, 2016 for International PCT Patent Application No. PCT/US2026/026825".

Agamatrix, Inc., Connected Health, http://agamatrix.com/products/connected-health/.

Alam, "Measurement of pH in Whole Blood by Near-Infrared Spectroscopy", Applied Spectroscopy, Mar. 1, 1999, pp. 316-324, vol. 53, issue 3—Abstract.

Bo, "Capillary method for measuring near-infrared spectra of microlitre volume liquids", Journal of Zhejiang University—3cience A, Feb. 1, 2007, pp. 171-175, vol. 8, Issue 2—Abstract.

Domjan, "Rapid Analysis of Whole Blood and Blood Serum Using near Infrared Spectroscopy", Journal of Near infrared Spectroscopy, Mar. 1, 1994, pp. 67-78, vol. 2, Issue 2—Abstract.

Engel, "Seventh Sense Biosystems Sucks in $10M for Simple Blood-Draw Device", Xconomy Boston, Nov. 18, 2016, http://www.xconomy.com/boston/2016/11/18/seventh-sense-biosysterns-sucks-in-10m-for-simple-blood-draw-device/#.

EP Supplementary European Search Report dated Oct. 22, 2018 for EP 16780499.

Gentag, NFC and Optical Skin Patches, http://gentag.com/nfc-skin-patches/.

Giardina et al., "The Multiple Functions of Hemoglobin", Criticai Reviews in Biochemistry and Molecular Biology, (Mar. 1, 1995), vol. 30, pp. 165-196, XP 055498007.

Huang, "Optimal waveband and mathematical model for analysis of human whole blood glucose by near infrared transmission spectroscopy", 5th International Symposium on Advanced Optical Manufacturing and Testing Technologies, Oct. 11, 2010, Dalian, China—Abstract.

International preliminary report on patentability dated Jan. 28, 2016 for PCT Application No. US2014/047097.

International Preliminary Report on Patentability for corresponding International Application No. PCT/US2017/060007, 8 pages (dated May 16, 2019).

International search report and written opinion dated Nov. 6, 2014 for PCT Application No. US2014/047097.

International Search Report and Written Opinion for corresponding International Application No. PCT/US2017/060007, 10 pages (dated Apr. 5, 2018).

International Search Report and Written Opinion for International Application No. PCT/US2017/023389, 19 pages (dated Jun. 1, 2017).

Kim, "Prediction of glucose in whole blood by near-infrared spectroscopy: Influence of wavelength region, preprocessing, and hemoglobin concentration", Journal of Biomedical Optics, Jul. 1, 2006, 11(4), 041128—Abstract.

Lafrance, "Measurement of lactate in whole human blood with near-infrared transmission spectroscopy", Talanta, Jul. 4, 2003, pp. 635-641, vol. 60, Issue 4, Elsevier—Abstract.

Lakshmi et al., "A simple slide test to assess erythrocyte aggregation in acute ST-elevated myocardial infarction and acute ischernic stroke: Its prognostic significance", Journal of Pathology and Microbiology, (Jan. 1, 2011), vol. 54, pp. 63-69, XP009507350.

Liu et al. "Application of a Genetic Algorithm to Quantitative Analysis of Overlapped FTIR Spectra", Spectroscopy Letters, vol. 34, No. 1, Jan. 22, 2001.

MDPI, Diagnostics—Open Access Journal of Medical Diagnosis, https://www.mdpi.com/journal/diagnostics/.

Murayama, "Near-infrared spectroscopy for liquids of microliter volume using capillaries with wall transmission", Analyst, 2003, Issue 7—Abstract.

Nemaura Medical, Improve blood sugar management, http://www.nemauramedical.com/sugarbeat/.

Rosenfeld, "New Skin Patch Monitors Glucose and Delivers Diabetes Drugs", Mar. 8, 2017, http://mentalfloss.com/article/93063/new-skin-patch-monitors-glucose-and-delivers-diabetes-drugs.

Staniszewska-Slezak et al. "Plasma biomarkers of pulmonary hypertension identified by Fourier transform infrared spectroscopy and principal component analysis", The Analyst, vol. 140, No. 7, Jan. 1, 2015.

Sund et al. "Cell Membrane Orientation Visualized by Polarized Total Internal Reflection by polarized total internal reflection fluorescence," Biophysical Journal, vol. 77, Issue 4, Oct. 1999, pp. 2266-2283.

(56) References Cited

OTHER PUBLICATIONS

Turza, "Near Infrared Analysis of Whole Blood and Plasma in Blood-Collecting Tubes", Journal of Near Infrared Spectroscopy, Jun. 1, 2006, pp. 147-153, vol. 14, Issue 3—Abstract.

Wan X, "Identification of Animal Whole Blood Based on Near Infrared Transmission Spectroscopy", PubMed, Guang Pu Xue Yu Guang Pu Fen Xi. Jan. 2016; 36(1):80-3. Chinese—Abstract.

* cited by examiner

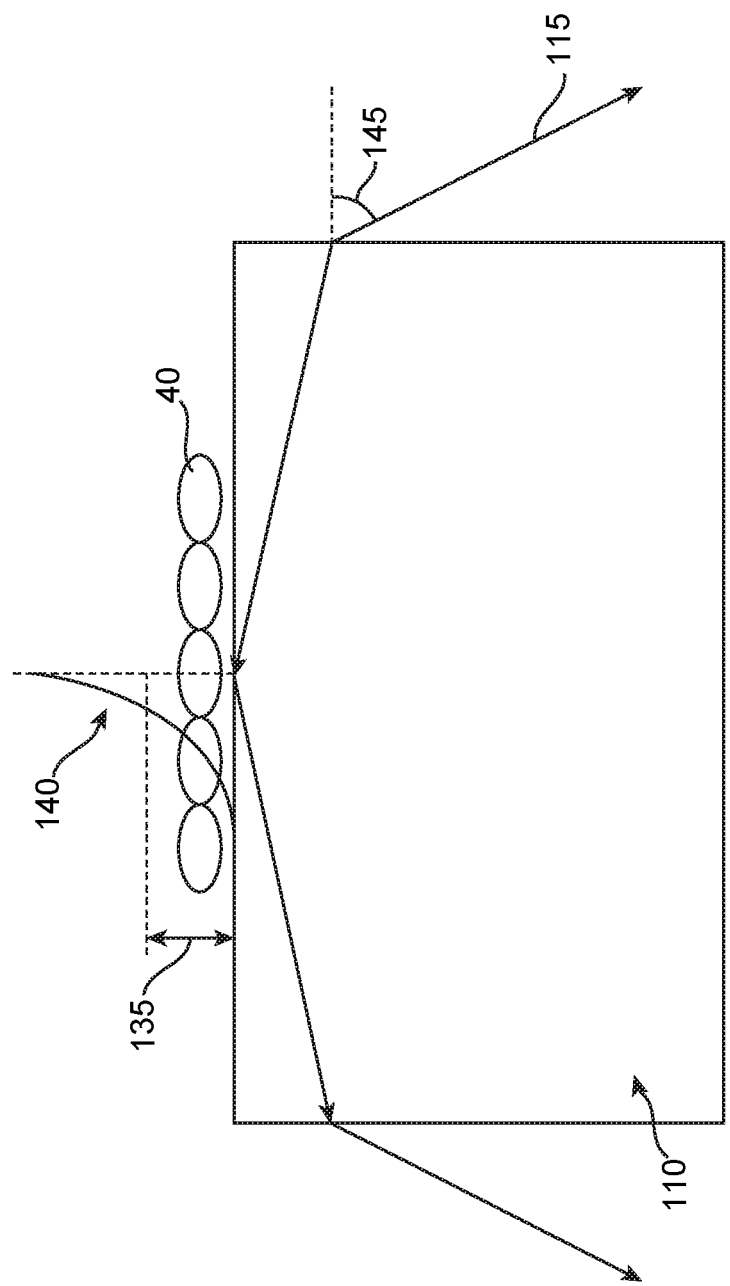

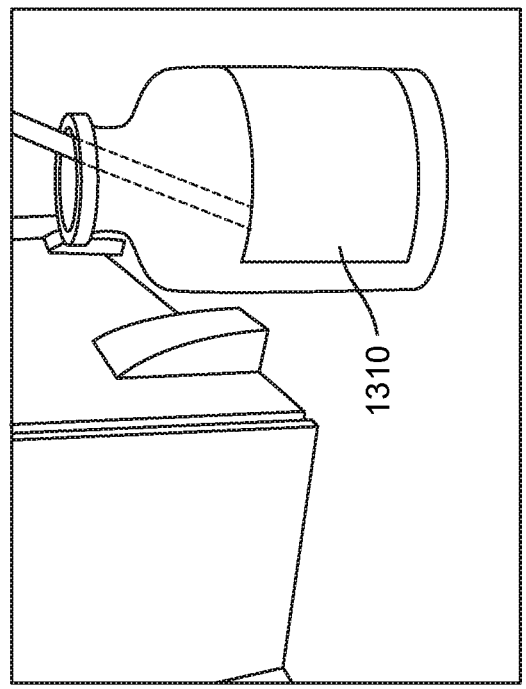
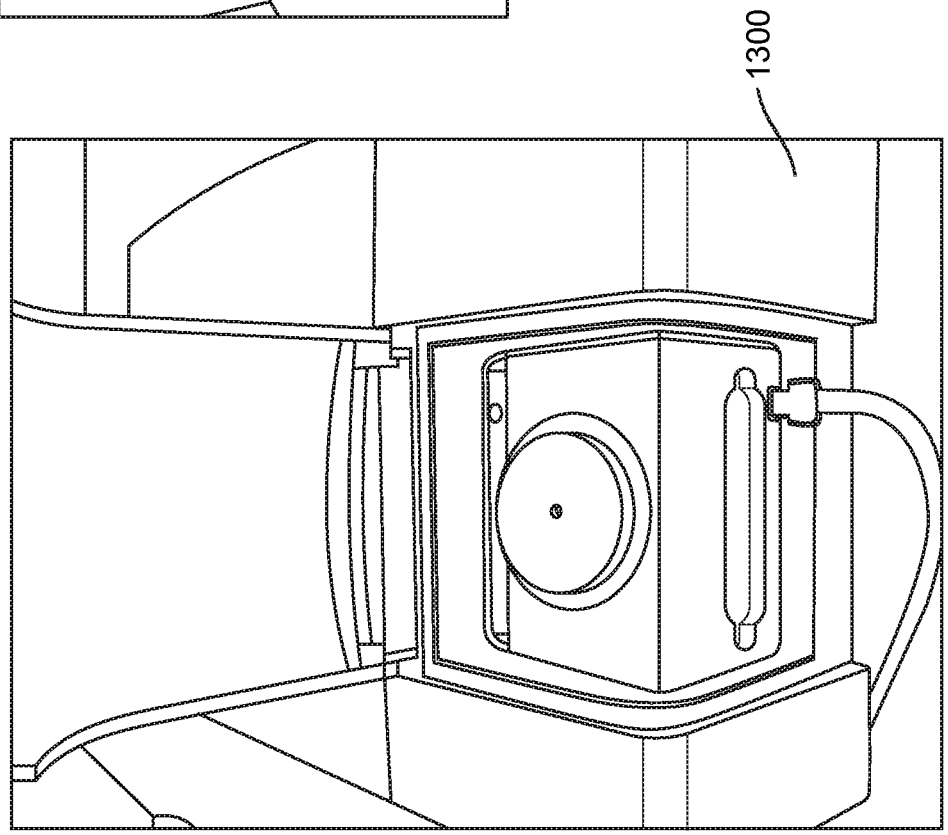
FIG. 13

METHOD AND APPARATUS FOR DETERMINING MARKERS OF HEALTH BY ANALYSIS OF BLOOD

CROSS-REFERENCE

The present application is a continuation of U.S. patent application Ser. No. 14/634,238, filed on Feb. 27, 2015, which claims priority to U.S. Provisional Patent Applications Nos. 61/946,494, filed on Feb. 28, 2014, 61/984,244, filed on Apr. 25, 2014, 62/005,522, filed on May 30, 2014, and 62/083,720, filed on Nov. 24, 2014, the entire disclosures of which are incorporated herein by reference.

The subject matter of the present application is related to PCT Applications Nos. PCT/US2015/018181, filed on Feb. 27, 2014, entitled "METHOD AND APPARATUS FOR DETERMINING MARKERS OF HEALTH BY ANALYSIS OF BLOOD" and PCT/US2014/047097, filed on Jul. 17, 2014, entitled "SPECTROSCOPIC MEASUREMENTS WITH PARALLEL ARRAY DETECTOR," the entire disclosures of which are incorporated herein by reference.

BACKGROUND

The field of the present invention is related to biomarkers of health, and more specifically to one or more of detecting, diagnosing, screening, tracking over time, or ruling out, one or more conditions such as high blood pressure and the harmful cardiovascular effects of high blood pressure. Examples of harmful effects of high blood pressure can include one or more of inflammation, coronary artery disease, stable plaques, unstable plaques, or other vascular factors related to the onset of heart disease and heart attack in humans.

Prior methods and apparatus of measuring biomarkers are less than ideal in at least some respects. Prior methods and apparatus of measuring blood pressure and diagnosing subjects can be less than ideal in at least some instances. Although blood pressure measurements can be used to assess the health of a subject and guide treatment, the prior methods and apparatus can be less than ideal. Work in relation to embodiments as described herein suggest that the prior peripheral blood pressure measurements can be less than ideally suited to guide therapy of a target tissue. For example, some organs such as the heart receive blood from the central vasculature and the prior peripheral blood pressure measurements may be less than ideally suited to guide therapy to such organs. Also, pressure measurements may be less than ideally suited to guide at least some treatments having a physiological effect on the subject's health, and measuring blood pressure is a somewhat indirect way of measuring subject physiology and characteristics that may be related to the tissues and blood of subject.

Modern blood pressure measurements are based on the sphygmomanometer, also referred to as a blood pressure cuff. The sphygmomanometer was invented by Samuel Siegfried Karl Ritter von Basch in 1881. A sphygmomanometer in the form of a cuff was patented in 1955 (GB740181). Although the sphygmomanometer remains a very important tool in medicine, it can have problems and deficiencies in at least some instances.

The sphygmomanometer in combination with a stethoscope allows a trained health professional to measure two characteristic values related to blood dynamics, the systolic and the diastolic pressure. The health care practitioner attaches the cuff around the subject upper arm over the brachial artery. Practitioner pumps up pressure in the cuff until the brachial artery is completely occluded. While listening to the brachial artery at the inside crease of the elbow, practitioner slowly releases pressure in the cuff. As the pressure falls, a whooshing sound is heard. These so-called Korotkoff sounds occur when blood flow first starts again in the artery. The pressure at which this sound is first heard is noted as the systolic blood pressure. The cuff pressure is released further until the Korotkoff sounds can no longer be heard. This is noted as the diastolic blood pressure. The peak pressure in the arteries is the systolic pressure, and the lowest pressure (at the resting phase of the cardiac cycle) is the diastolic pressure. The systolic and diastolic pressure measurements have become the medical standard of care for diagnosing high blood pressure.

Although helpful in diagnosing high blood pressure, the systolic and diastolic blood pressure measurements can result in less than ideal measurements that may be related to one or more of the following:

Observer error;
Systematic intraobserver and interobserver errors;
Terminal digit preference, rounding to favorite digit;
Observer prejudice;
White coat hypertension—high only in doctor's office;
Masked hypertension—normal in office, high at other times of day;
Instrument error;
Defective control valve;
Improper fit of cuff, too large or too small;
Inadequate length of tubing;
Connections not airtight;
Position of manometer causes reading error;
Placement of cuff error;
Diastolic dilemma—muffling of sounds can occur 10 mm before complete disappearance;
Two arms can exhibit different readings; or
Deflation too rapid.

These errors can lead to inaccurate blood pressure readings that may be related to improper diagnoses in at least some instances. For example, errors as large as 20 mm Hg may occur in at least some instances.

If a subject is incorrectly diagnosed as having high blood pressure when actually having low blood pressure, this person may be placed on a daily blood pressure medication. Many of these medications may have side effects, and more people than would be ideal can be subjected to the side effects of blood pressure medications. Also, blood pressure measurement errors may result in a person who actually has high blood pressure being misdiagnosed as having low blood pressure. An incorrect diagnosis for a subject with high blood pressure can result in that subject not receiving appropriate medication, such that the high blood pressure may not be untreated in at least some instances. Inappropriate management of high blood pressure can result in injury to the subject and may even be fatal in at least some instances, and it would be helpful to have fewer misdiagnoses of high blood pressure.

Blood pressure measurements located at the brachial artery may be less than ideally suited to guide treatment. For example, the brachial artery is located away from the aorta other central blood vessels and provides a less than ideal determination of central blood pressure, and measuring systolic and diastolic pressure in the brachial artery of the arm may be less than ideally suited to diagnose central high blood pressure that can be related to organ damage in at least some instances. Although beta blocker medications can lower peripheral blood pressure and blood pressure of the arteries in the arm, these medications may not lower central blood pressure in at least some instances, and people treated with beta blockers having normal brachial pressure may still experience heart failure.

Work in relation to embodiments suggest that it would desirable to have a record of blood pressure and of cardiovascular health over a period of time, rather than an instantaneous measurement like brachial cuff pressure.

Although blood chemistry is the gold standard for screening, diagnosis, and therapy in health wellness and medicine, the prior methods are less than ideal in at least some respects. Currently, a blood panel is requested by a physician and the patient is instructed to travel to a blood laboratory where a phlebotomist can draw blood from the antecubital vein into a series of special collection tubes. The blood is then sent to a central blood chemistry laboratory where it is chemically analyzed using numerous wet chemical assays that have been developed and validated over the years. More recently, a small portion of these tests can be performed in a physician's office using specialized machines employing enzymatic assays. Such delivery of blood to various locations can be less than ideal.

Blood chemistry testing is rapidly moving to the point-of-care for many reasons. The biggest of these are cost and compliance. Blood testing in the POC and eventually in the home dives down healthcare costs, is trackable and reportable, is immediate and actionable, sticky, and socially supportive compared to central lab testing. But the problem that needs to be overcome is that central lab methods generally do not translate to the POC and the home, since they require much wet chemistry and expensive instrumentation.

Measurement and detection of biomarkers can be done in conjunction with modern computers and software. These prior computers and software can less than ideally solve the technical problem of the detection and identification of biomarkers related health of a subject. The prior software and algorithms can be less than ideally suited to determine the health of a subject in response to data such as spectral data.

In light of the above, it would be desirable to provide improved methods and apparatus for measuring biomarkers of a patient, such as biomarkers useful in determining blood pressure. Ideally such methods and apparatus would provide a more accurate reading of blood pressure with less variability and fewer false negatives and false positives for high blood pressure, provide a more accurate determination of central blood pressure, allow improved treatment and management of blood pressure, and provide an indicator of blood pressure and cardiovascular health over time.

SUMMARY

Embodiments are directed to measurement of samples in order to determine one or more biomarkers related to health. In many embodiments, the one or more biomarkers comprises a biomarker of a cell membrane, such as a biomarker of a red blood cell membrane. The biomarker may comprise one or more of a component of a cell membrane, or a substance such as a molecule that interacts with the membrane.

Embodiments can provide improved methods and apparatus of identifying high blood pressure of a subject. In many embodiments, one or more biomarkers of high blood pressure are measured in order to identify high blood pressure of the subject. Identifying the blood pressure of a subject based on one or more biomarkers has the advantage of being more accurate and less susceptible to short term fluctuations in physiology and user variability at the time of the measurement. In many embodiments, the response of the biomarker to blood pressure occurs over the course of at least an hour, for example at least a day, such that the high blood pressure identification is based on a cumulative effect of physiology of the subject over a period of time such as an hour, a day or weeks, as opposed to the very short amount of time during which a blood pressure measurement is made at a clinic and can fluctuate. The methods and apparatus of identifying high blood pressure with biomarkers as disclosed herein have the advantage of providing improved treatment of the subject, as the identified biomarker can be related to an effect of the high blood pressure on the subject, such as a biomarker corresponding to central blood pressure. The sample can be subjected to increases in one or more of pressure or temperatures, and changes in the blood sample measured over time.

In many embodiments, the apparatus comprises a first measurement channel to measure the blood sample near a measurement surface with an evanescent wave of an internally reflected light beam, and a second measurement channel to measure the blood sample through a thickness of the sample with a transmission measurement. The transmission measurement can be measured through the measurement surface and the thickness of the sample, such that an internally reflected measurement beam and a transmission measurement beam overlap at least partially. In many embodiments, the evanescent wave measurement comprises an evanescent wave spectroscopy measurement and the transmission measurement comprises a transmission spectroscopy measurement. While the measurement surface and first channel and the second channel can be configured in many ways, in many embodiments the measurement surface comprises a measurement surface of a Dove prism and the internally reflected measurement beam is transmitted through inclined surfaces on opposing ends of the Dove prism.

In many embodiments, the blood sample comprises a first component having red blood cells or clotted cells and a second component comprising plasma or serum and each of the first component and the second component is measured. Each of the components can be measured with the evanescent wave spectroscopy and the transmission spectroscopy in order to provide four measurement channels.

In a first aspect, embodiments provide an apparatus to identify high blood pressure of a subject. The apparatus comprises a processor comprising instructions to identify a blood pressure biomarker of a blood sample of the subject.

In another aspect, embodiments provide a method of identifying high blood pressure of a subject. A blood pressure biomarker of a blood sample of the subject is identified.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIG. 10 shows light entering germanium (index of refraction n=4) at an incident angle of 80 degrees, resulting in total internal reflection and a very shallow 1/e penetration depth of the resulting evanescent wave into the sample, in accordance with embodiments;

FIG. 13 shows a commercially available spectroscopy apparatus suitable for combination, in accordance with embodiments;

DETAILED DESCRIPTION

Figure 1:
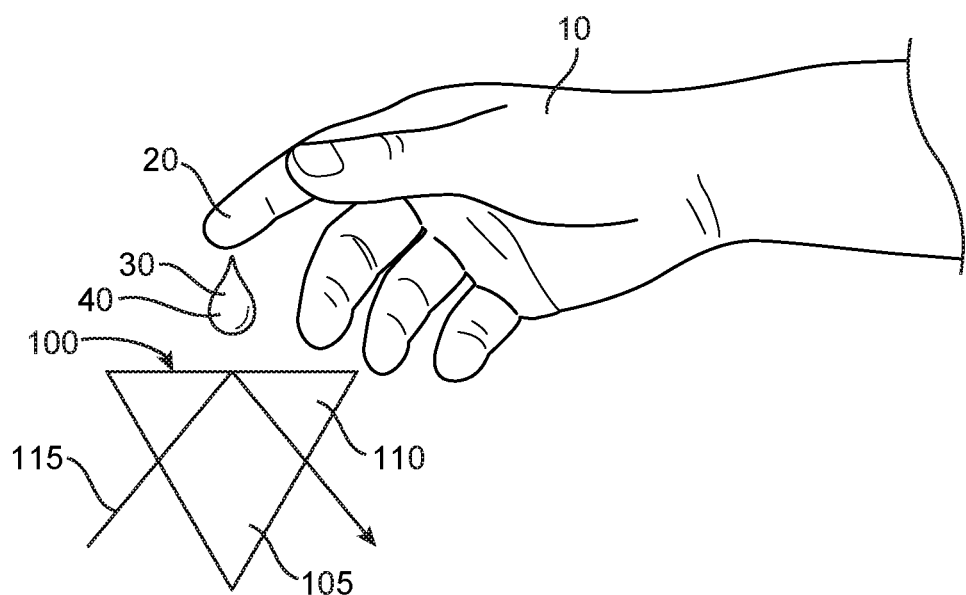
FIG. 1 shows a blood sample from a subject being placed on a measurement surface in order to measure blood pressure biomarkers, in accordance with embodiments.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein.

The embodiments disclosed herein can be combined in one or more of many ways to provide improved measurements of blood samples from a subject.

As used herein like characters identify like elements.

In many embodiments, an evanescent wave comprises a near-field wave with an intensity having an exponential decay as a function of the distance from the boundary at which the wave was formed. Materials place on a surface can interact with the near field wave, with or without absorption, for example. This use of the evanescent near field wave can provide improved signal to noise ratios when measuring the membrane of cells such as the red blood cell. The localization of the evanescent wave intensity profile to the cell membrane can provide an effective amplification of the measured signal.

The shape of the red blood cell (hereinafter "RBC") is particularly well suited for evanescent wave measurement as disclosed herein. The red blood cell membrane comprises a biconcave disk shape having a flattened region along the long dimension and an indentation near center, which allows the red blood cells to settle onto a measurement substrate such that the long dimension of the red blood cell extends in a direction along the surface of the substrate, such that a significant portion of the red blood cell membrane along the long dimension can be exposed to the evanescent wave and measured. The red blood cell membrane comprises proteins and lipids, and this structure provides properties for physiological cell function such as deformability and stability. Approximately 2.4 million new erythrocytes are produced per second. The cells develop in the bone marrow and circulate for about 100-120 days in the body before their components are recycled by macrophages. The deformability of the human red blood cell results from the dynamic interaction of the phospholipid bilayer plasma membrane and the structural spectrin molecular network. Adenosine 5'-triphosphate (ATP) facilitates remodeling in the coupled lipid and spectrin membranes.

As used herein, a red blood cell encompasses an erythrocyte.

The embodiments disclosed herein can be combined in one or more of many ways.

In many embodiments, the detection and diagnosis of disease and wellness through reagent-less whole cell in vitro analysis of changes in the erythrocyte membrane from a single drop of blood collect via a lancing device is provided.

The embodiments as disclosed herein are particularly well suited for performing spectroscopic analysis of RBC proteins, lipids, and combinations thereof, for example for assessing the risk of cardiovascular diseases. The spectroscopic analysis can be performed without in vitro enzymatic analysis, and without lysing the cells or pretreating samples, for example.

In many embodiments, spectroscopic analysis of the RBC for detecting cell stress and changes in cell morphology associated with hypertension allows retroactive assessment of past cell damage due to elevated blood pressure. The retroactive assessment can significantly decrease the need for continuous blood pressure measurement, and in many embodiments can eliminate bias due to patient's mood or emotional state. The membrane of the erythrocyte undergoes molecular changes, or remodeling, in hypertension. These changes appear to be a response to increased shear forces on the cells as blood pressure increases. When erythrocytes undergo shear stress in constricted vessels, they can release ATP, which causes the vessel walls to relax and dilate so as to promote normal blood flow.

In many embodiments, the RBC is used as messenger cell to report disease markers which the RBC encounters during circulation.

The apparatus embodiments as disclosed herein are particularly well suited for performing analysis of red blood cells as disclosed herein.

In many embodiments, the apparatus comprises a user interface and one or more databases for performing one or more of the analyses as disclosed herein.

In many embodiments, the red blood cells (erythrocytes) are separated, for example with standard method, such as centrifuge. Alternatively or in combination, whole blood is separated gravimetrically such that the relatively heavier erythrocytes fall onto the sampling surface as described herein.

While the analytical method and apparatus can be configured and performed in many ways, in many embodiments, the methods and apparatus are configured for one or more of measurement of mechanical or molecular properties via infrared, near-infrared, UV, Raman, Surface enhanced Raman, resonance Raman, fluorescence, NMR, terahertz, far infrared, circular dichroism) or through a mechanical test (mechanical stiffness), or through a thermal property analysis (thermal gravimetric analysis TGA). In many embodiments, the analytical methods and apparatus comprise molecular spectroscopy methods and apparatus, such as one or more of infrared, Raman or near-infrared spectroscopy, for example. The methods and apparatus can be configured to perform one or more of measurements in transmission, absorbance, photo acoustic, or reflection mode, in internal reflection mode, for example.

In many embodiments, the erythrocyte membrane is measured for changes. The erythrocyte membrane can undergo molecular changes during one or more of many disease states. Examples of examples of membrane changes related to disease states that can be measured in accordance with embodiments include:

Average blood glucose (membrane protein glycosylation)
High blood pressure (membrane elasticity)
Inflammation (fibrinogen on surface of membrane)
Cerebrovascular disorders (fibrinogen binding on RBC membrane)
Thrombosis (erythrocyte agglomeration)
Unstable plaque (lipid on surface of cell membrane)
Acetylsalicylic Acid (ASA) therapy (cell membrane • slippery-ness •)
Malaria (cell deformation)
Dehydration (membrane water content)
Sepsis (erythrocyte sedimentation rate)
Blood bank aging
Myocardial infarction (rigidity)
Diabetes (rigidity)
Sickle cell anemia (deformation)
Malaria (deformation, lipid profile)
Exercise oxidative stress (loss of C=C bonds)
Antioxidant level (ceruloplasmin level)
Drug uptake (Codeine, chlorpromazine, imipramine, mefloquine, and pyrimethamine, acetazolamide, methazolamide, and chlorthalidone and the ocular pressure reducing agent, dorzolamide)
Hemolytic Anemia (lipid ratios)
Preeclampsia (membrane rigidity)
Ionic balance (protein stricture)
pH (protein structure)
Alzheimers (AD) (levels of proteins in membrane skeleton)
Malnutrition (kwashiorkor and marasmus) (elevated Cholesterol/phospholipid ratio)
Hereditary Spherocytosis (deficiency of ankyrin, spectrin and protein 4.2)
Hereditary Elliptocytosis (spectrin defects, glycophorin deficiency)
Acanthocytosis (free cholesterol/phospholipid ratio)
Alcohol (association with lipid bilayer)
Coumadin therapy dosimetry
Whole blood viscosity In many embodiments, the presence of undesirable effects of high blood pressure on the vascular system can be identified in one or more of many ways. In many embodiments, an amount of one or more biomarkers of the blood can measured in order to identify high blood pressure of the subject. For example, a level of biomarker in the blood can provide an indication of high blood pressure, and in many embodiments an amount of biomarker from a blood sample above a threshold amount can identify the subject as having high blood pressure. In many embodiments, the methods and apparatus to measure the biomarker can provide an improved identification of blood pressure with fewer false positives and false negatives than at least some prior cuff measurements of the brachial artery, for example.

Work in relation to embodiments as described herein suggests that the red blood cells (hereinafter "RBCs") can be involved in the signaling of high blood pressure, and the methods and apparatus as described herein can measure one or more RBC markers related to the RBC signaling of high blood pressure. For example, increased mechanical pressure on the RBCs can induce the RBCs to release one or more biomarkers such ATP, for example. The released ATP may signal changes to the blood vessel walls, or transmit signals to the blood vessel walls, or both, for example. Alternatively or in combination, cell membranes of the RBCs may stiffen, thereby indicating chemical changes in the cell membrane of the RBC. Although these effects may not yet be fully understood, the RBC signaling, reporting, and responding to high blood pressure can be combined with measurements of the RBCs to identify high blood pressure of the subject, in accordance with many embodiments as described herein.

In many embodiments disclosed herein, a biomarker provides a record of blood pressure and of cardiovascular health over a period of time, rather than an instantaneous measurement like brachial cuff pressure. In many embodiments, the metric or biomarker is related to recent history of high blood pressure would be. For example, a time period of 90-120 days can be particularly useful for reasons similar to that Hemoglobin A1c marker is useful for controlling blood sugar in diabetes. Such a marker can be especially useful for providing health and lifestyle advice to a patient. Such a marker can also be especially useful for ensuring the proper dosage and efficacy of a drug used to treat high blood pressure, and for determining compliance with taking a therapeutic agent, in accordance with embodiments disclosed herein.

In many embodiments, RBCs are large and as they travel through the vasculature, can come in contact with vessel walls that leave chemical residue on the RBCs, for example. In this manner the RBC membrane comprises markers to identify and determine the chemistry of the lining of the vessels walls. In many embodiments, when this transfer occurs, the RBCs comprise a marker of the atherosclerotic plaque that can be used to report the presence of atherosclerotic plaques within the blood vessels. The corresponding chemical spectrum obtained from the RBCs can be used to differentiate the presence of an unstable plaque from a stable plaque, which spectra are chemically distinct, for example.

In many embodiments, atherosclerotic plaques comprise one or more of three categories: foam-cell rich, lipid-rich, or collagen-rich. In many embodiments, the distinct chemistry of each plaque leaves distinct residue patterns on the outside of the red blood cell membrane. Lipid-rich plaques have been associated with dangerous unstable plaques. The residual material of the one or more plaques can be deposited on the red blood cell membrane and measured in accordance with embodiments described herein.

In some embodiments, a substance is injected into the blood. The substance may comprise one or more of mild abrasive, stickiness, or affinity to atherosclerotic plaques, for example. The affinity can be specific to one or more of the plaques as described herein. After a period of time, this substance can be recovered from blood via a blood draw. By measuring the exterior of these substance particles, the presence of unstable plaques can be detected. The substance may comprise one or more of many known substances such as one or more of many known sugars, for example.

In many embodiments, the abrasive substance comprises a non-toxic material that causes alteration to the blood to in order to cause a heightened but temporary level of abrasion and inflammation in the coronary arteries. In many embodiments, the substance clears from the blood in a short time after the measurement is made. An example of a suitable candidate substance is a sugar, such as one or more of glucose, fructose, or mannose, for example. High blood sugar can be a known condition in diabetes. Although sugar is known to cause inflammation in the vasculature and can increase agglomeration in red blood cells, sugar clears naturally from the blood system, since it is metabolized readily.

In many subjects, the lifetime of an RBC can be approximately 90 to 120 days. The changes of the RBC due to high blood pressure can be related to the relatively recent history of high blood pressure over the course of the lifetime of the RBC. If a medication is taken for high blood pressure, the characteristics of the RBCs can revert to normal relatively quickly because of the rapid turnover of these cells, for example. Alternatively or in combination, an amount of the one or more signaling biomarkers stored on or within the RBC, such as ATP, can be related to blood pressure of the subject, for example related to shear stress of the RBC during cardiac cycling of the RBC.

There may be changes in other blood constituents as well. For example, stiffened RBCs can be somewhat abrasive in the vessels, which can lead to inflammation and additional biomarkers suitable for measurement in accordance with embodiments disclosed herein. While many biomarkers can be measured in accordance with embodiments disclosed herein, an example of such biomarker suitable for measurement is C—reactive protein (hereinafter "CRP"), for example.

Proteins in blood can also change conformation in response to pressure. Proteins such as albumin which exists in high concentration in blood may also be measured in order to identify high blood pressure of a subject.

In many embodiments, one or more components of blood are analyzed such as the serum component of blood, or the cellular component of blood, or both, in order to determine the presence of biomarkers of high blood pressure.

In many embodiments, and amount of blood such as a drop of blood is provided for analysis. For example, an amount of blood can be provided into a capillary tube which has been heparinized. The RBCs can be caused to separate from the serum. An instrument configured in accordance with embodiments as described herein can pass a beam of light may through the capillary tube, to measure one or more of the serum portion, or the cellular portion, or both, for example. The capillary tube can be pressurized, and one or more of the constituents in blood such as proteins may respond differently to pressure when the blood has been subjected to high blood pressure, such that a differential measurement obtained. For example, a first measurement can be obtained at first pressure and a second measurement obtained a second higher pressure higher than the first pressure. For example, the first pressure can be approximately atmospheric pressure, and the second pressure can be greater than atmospheric pressure. In many embodiments, pressures as high as 600 MPa can be used to cause the unraveling and denaturation of proteins in the blood. The rates and dynamics of these protein changes in response to applied external pressure can be correlated with the blood having been subjected to high blood pressure previously within the subject.

FIG. 1 shows a blood sample 30 from a subject being placed on a measurement surface 100 in order to measure blood pressure biomarkers. The blood sample is obtained from the subject. The subject has a hand 10 from which a blood sample can be obtained, for example. Although a hand is shown the blood sample can be obtained in one or more of many known ways. The blood sample is placed on a measurement surface.

In many embodiments, the measurement surface on which the red blood cells 40 are placed comprises an optical prism 110 for the purpose of channeling measurement light 115 under the blood, through the prism, by internal reflection. Internal reflection spectroscopy can make spectroscopic measurements at a shallow depth beyond the prism surface, since an evanescent wave is set up at that interface. This rapidly diminishing evanescent wave rapidly diminishes with distance away from the prism surface. The resulting spectrum is thereby resulting from only the material that is resting closest to the prism. In our blood cell sample, the spectrum would contain information mainly about the cell membrane and not the cytoplasm. One proposed mechanism of action for correlating with blood pressure is changes in the cell membrane of the red blood cells as a biomarker. In many embodiments, the membrane spectrum contains spectra of one or more biomarkers having amounts corresponding to the blood pressure of the subject.

The measurement surface can be configured in one or more of many ways to measure the sample. In many embodiments, the measurement surface comprises a flat surface of an optically transmissive material such as Silicon or Germanium, for example. The optically transmissive material can be shaped in one or more of many ways to provide the measurement surface as described herein. For example, the optically transmissive material may comprise a prism, a flat plate, a cube, a rectangle or a Dove prism, for example.

In many embodiments, the sample is measured near the measurement surface with total internal reflection spectroscopy (hereinafter "TIR"). With TIR, the measurement light beam is directed toward the surface at an angle so as to provide total internal reflection of the light beam from the measurement surface. Although the light beam is reflected internally from the surface, the light beam can interact with the sample on the opposite side of the surface from the light beam with an evanescent wave of the light beam. The evanescent wave of the light beam extends beyond the measurement surface by a distance related to the wavelength of the measurement light beam. In many embodiments, the evanescent wave extends beyond the surface so as to provide a penetration depth of about $0.1\lambda$ into the sample place on the measurement surface, where $\lambda$ is the wavelength of light. The TIR light may comprise one or more of visible light, near-infrared light, mid-infrared light or far infrared light, for example. In many embodiments, the light used comprises mid-infrared light having one or more wavelengths within a range from about 2 μm (micrometer) to about 20 μm, for example. The one or more wavelengths of light may comprise a plurality of wavelengths of light to scan to a plurality of depths of the sample.

With TIR spectroscopy, the depth of the measurement is related to the measurement wavelength such that the membranes of red blood cells on or near the surface can be measured. With a 2 μm wavelength, the penetration depth is about 0.2 μm such the penetration depth of the TIR measurement does not extend beyond a thickness of a red blood cell. With a 20 μm wavelength, the penetration depth is about 2 μm such the penetration depth of the TIR measurement corresponds to the approximate a thickness of a red blood cell.

Figure 2:
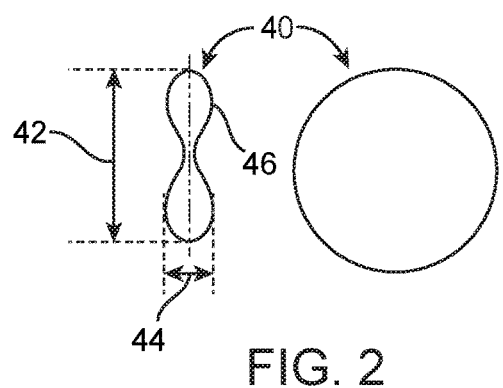
FIG. 2 shows a side profile view and corresponding dimensions of a red blood cell, in accordance with embodiments.

FIG. 2 shows a side profile view and corresponding dimensions of a red blood cell 40. The red blood cell comprises an approximately toroidal shape having a long dimension along an elongate axis defining a length 42 of the red blood cell and a short dimension along a transverse axis defining a thickness 44 of the red blood cell. The length of the red blood cell is approximately 7 (seven) microns and the width is approximately 2 (two) microns.

When the red blood cell is forced through an opening with blood pressure such as an opening of a capillary channel sized smaller than the red blood cell, the shape of the red blood cell can change to allow the red blood cell to pass, and one or more biomarkers such as ATP can be released. Alternatively or in combination, high central blood pressure can result in one or more of deformation of the red blood cell or surface changes to the red blood cell related to the high central blood pressure of the subject, and the biomarkers corresponding to these changes can be measured in accordance with embodiments disclosed herein.

In many embodiments, the methods and apparatus are configured to measure the surface of the red blood cells and identify one or more components of the red blood cells specifically. A sampling and measurement system can be configured to first separate cells from serum or plasma through sedimentation, then place a sample of blood cells onto one measuring stage and a sample of serum onto another measuring stage, for example, so as to provide separate measurements. The volume of blood sample can be small, such as a drop that could be obtained by a lancet at a finger. The stage holding the blood cells may comprise a horizontal surface on which the blood cells can be placed as described herein. The measuring stage holding the serum or plasma may comprise another measuring surface for TIR or transmission measurements as described herein, and combinations thereof, for example.

Figure 3:
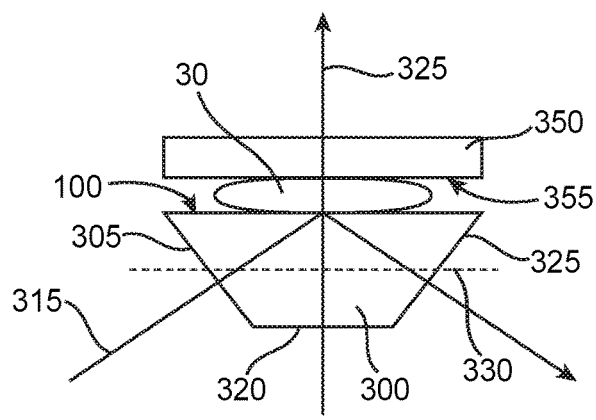
FIG. 3 shows measurement of a blood sample with a Dove prism in order to identify high blood pressure biomarkers with a first measurement channel and a second measurement channel, in accordance with embodiments.

FIG. 3 shows measurement of a blood sample 30 with a Dove prism 300 in order to identify high blood pressure biomarkers with a first measurement channel and a second measurement channel. In many embodiments, the first measurement channel comprises a TIR measurement channel, and the second measurement channel comprises an optical transmission channel extending through a thickness of the sample. The Dove prism can provide a first inclined surface 305 and a second inclined surface 310 that allow the first measurement light beam 315 to be totally internally reflected and directed to the inclined surfaces at an angle that decreases reflection from the inclined surfaces. The Dove prism, like many shapes, comprises a surface 320 opposite the TIR measurement surface 100 that receives a second measurement beam 325 for transmission through the measurement surface and bulk of the sample. The Dove prism comprises an elongate axis 330 extending axially through the inclined surfaces and between the measurement surface and the opposing surface.

In many embodiments, a transparent movable support 350 is provided to shape an upper surface of the sample for transmission of the second measurement light beam. The transparent movable support may comprise a thickness suitable for pressurizing the sample with a pressure surface 355 for measurements as described herein. Alternatively, the transparent movable support can be thin to shape the blood sample without pressurizing the blood sample, for example a microscope slide.

Although a Dove prism is shown, the optical system can be configured in one or more of many ways with one or more of prisms, cubes, rhomboids or parallelepipeds, for example.

Figure 4:
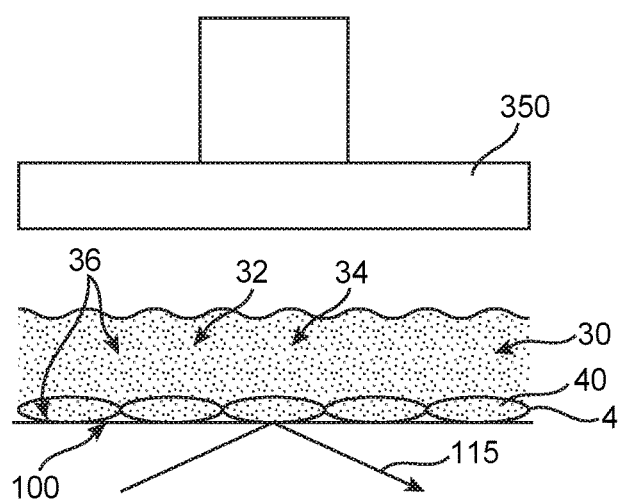
FIG. 4 shows red blood cells located on a measurement surface to measure the red blood cells with an evanescent wave and identify high blood pressure biomarkers of the red blood cell membranes, in accordance with embodiments.

FIG. 4 shows red blood cells 40 located on a measurement surface 100 to measure the red blood cells with an evanescent wave generated from the total internal reflection of the measurement light beam 115 in order to identify high blood pressure biomarkers of the red blood cell membranes 46, in accordance with embodiments.

The blood sample 30 can be prepared in one or more of many ways for placement on the measurement surface. In some embodiments, the measurement surface or a solution combined with the blood sample comprises a clotting antagonist to inhibit blood clotting, in order to allow measurement of red blood cells and to separate the blood cells into a first component having a greater number of red blood cells and a second component having a greater amount of plasma as compared to the sample as drawn from the subject. Alternatively, the blood sample can be allowed to clot such that the sample comprises a first clot component and a second serum component, in which the clotting factors of the plasma have been substantially depleted to form the blood clot.

In many embodiments, the components of the serum 32 or plasma 34 and the blood cells 40 are each measured. In many embodiments, the plasma and blood cells can be separated at least partially so as to provide different measurements for each, for example separate simultaneous measurements of each.

In many embodiments, a second beam of light can be transmitted through the blood sample. In these embodiments, a spectrum representative of the bulk of the measurement cell is obtained. The second stage can be a similar internal reflection prism to measure the blood serum both by internal reflection and by transmission. The transmission measurement represents the bulk of the serum or plasma. In many embodiments, the proteins 36 in the blood can begin to coat the prism as time progresses. Therefore the internal reflection channel becomes a way of measuring the proteins in blood with greater intensity than could be measured in the bulk serum sample. Alternatively or in combination, the red blood cells can sediment downward onto the measurement surface, and the membranes of the red blood cells within the penetration depth of the evanescent wave can be measured and the bulk of the plasma measured with the transmission beam.

In many embodiments, two measurement cells on two measurement stages can be used to measure the two components of blood separately such that four measurements from four independent measurement channels are provided. The evanescent wave measurements can be combined with the transmission measurements so as to provide four different spectral channels. Each of these channels can be interrogated with different wavelengths of light, from the visible to the far infrared region.

In many embodiments, each of these channels is measured as a function of time to follow changes in the blood cells and the serum and/or plasma with time. During this time, the samples can be subjected to different temperatures by embedding a heating or cooling element into the stages. Alternatively or in combination, a movable transparent support 350 comprising an optical window can be added on top of the blood cell and serum or plasma sample. This support comprising the window can be mounted in a frame which can create a pressure seal at the stage. In many embodiments, a high external pressure can be exerted on the blood cells and blood serum. Pressures of up to 600 MPa can be used in order to denature and change the structure of the components and specifically proteins in the sample, for example. In many embodiments, these dynamic measurements can identify differences among biomarkers in blood that has been exposed to high blood pressure versus blood from subject without high blood pressure, for example.

Figure 5:
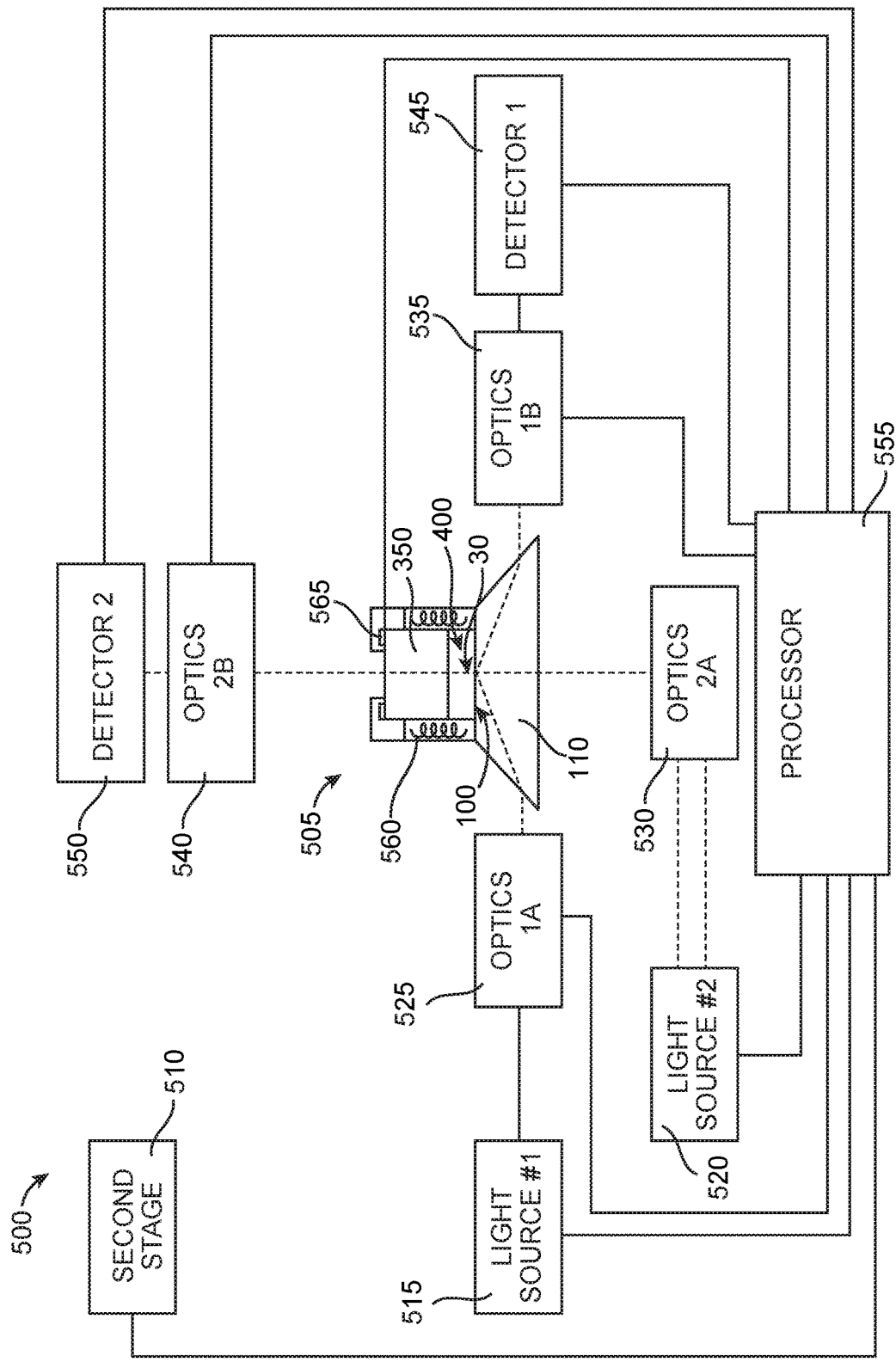
FIG. 5 shows an apparatus to measure blood pressure biomarkers, in accordance with embodiments.

FIG. 5 shows an apparatus 500 to measure blood pressure biomarkers. The apparatus comprises a first measurement stage 505 comprising a surface 100 to receive a blood sample 30 of a subject. In many embodiments, the apparatus comprises a second stage 510 to receive a second sample of the subject as described herein. For example, the first sample may comprise a red blood cell component and the second sample may comprise a plasma component, in which the red blood cell component comprises a greater amount of red blood cells than the initial sample from the subject and the plasma component comprises a greater amount of plasma than the initial sample from the subject, for example. The first measurement stage and the second measurement stage may comprise similar components and can be coupled to light sources, optics and detectors similarly and in accordance with embodiments as described herein.

The apparatus to identify blood pressure biomarkers comprises one or more light sources, for example first light source 515 and second light source 520. The apparatus comprises one or more input optics optically coupled to the light sources so as to receive light from the light sources, for example first input optics 525 for TIR measurements and second input optics 530 for bulk transmission measurements. The apparatus comprises one or more output optics optically coupled to the sample container to receive the light from the sample, for example first output optics 535 to receive the TIR light and second output optics 540 to receive the transmission light. The one or more output optics are optically coupled to one or more detectors, for example first detector 545 coupled to output optics 535 and second detector 550 coupled to output optics 540.

The components of the apparatus 500 can be coupled to a processor 555 comprising instructions to control the measurement of the sample, for example of the first sample stage. In many embodiments, the processor is configured and coupled to the one or more light sources, the input optics, the output optics and the detectors in order to measure optical spectroscopy of the sample. The processor can be coupled to the first light source to control the generation of light for TIR measurements. The processor can be coupled to the second light source to control the generation of light for the transmission measurements. The processor can be coupled to the first input optics and first output optics to control the input and output optics of the TIR measurements as appropriate, for example when the input and output optics comprise one or more movable or electro-optical components such as shutters, gratings, etalons, mirrors, lenses, Bragg cells, prisms or wavelength selective filters, for example. The processor can be coupled to second input optics and second output optics to control the input and output optics of the bulk transmission measurements as appropriate, for example when the input and output optics comprise one or more movable or electro-optical components such as shutters, gratings, etalons, mirrors, lenses, Bragg cells, prisms or wavelength selective filters, for example.

The processor can be coupled to the first detector to measure the light from the TIR measurement and the second detector to measure light from the bulk transmission measurement. The detectors of the apparatus 500 such as the first detector 545 and second detector 550 may comprise one or more of many known detectors such as a one or more of photodiode, a phototransistor, a charge coupled device (hereinafter "CCD") array, or conducting metal oxide semiconductor arrays (hereinafter "CMOS" arrays), for example. The detectors or the processor may comprise analog to digital conversion circuitry to provide a digital measurement signal to the processor.

The light sources of the apparatus 500 such as the first light source 515 and second light source 520 may comprise one or more of many known light sources such as lamps, diodes, lasers, laser diodes, tunable lasers, optical parametric oscillators, providing a suitable wavelength of light, for example in the mid infrared as described herein. In many embodiments, one or more of the light source or the input optics is coupled to the processor to vary the wavelength of light, for example.

The apparatus 500 may comprise similar components connected to the processor for the second measurement stage. Alternatively, the first stage and the second can be interchangeable such that the first measurement stage can be removed and replaced with the second measurement stage.

The first measurement stage may comprise the prism 110, sample container 400 and movable transparent support 350 as described herein. The stage may comprise a coil 560 embedded in the container to heat the sample 30 as described herein, and an actuator 565 coupled to the movable transparent support to pressurize the sample. A pressure sensor and a temperature sensor can also be provided on the measurement stage to monitor the pressure and the temperature of the sample. The prism may comprise a Dove prism having the measurement surface 100 to provide the evanescent wave and bulk transmission measurements as described herein.

The processor comprises a tangible medium to store the instructions, such as one or more of random access memory (hereinafter "RAM"), read only memory (hereinafter "ROM"), flash memory, gate array logic, a gate array, or a field programmable gate array, for example. The processor may comprise a processor system comprising a plurality of processor in communication with each other, for example. In many embodiments the processors communicate with each other with one or more known communication methods and apparatus such as wireless communication, a shared bus, a shared drive, serial communication, the Internet, and combinations thereof, for example.

The changes in one or more components of blood disclosed herein can be measured in one or more of many ways. For example, the changes can be detected using a one or more of many types of chemical analyses, such as spectroscopy and spectrometry, for example. In many embodiments, spectroscopy methods and apparatus are configured for measuring blood components, such as changes in molecular conformation in blood cell membranes and blood proteins. Examples of suitable spectroscopy methods and apparatus suitable for incorporation in accordance with embodiments disclosed herein include one or more of vibrational spectroscopy, either mid-infrared or near-infrared absorption or reflection spectroscopy, or Raman spectroscopy, and combinations thereof. In many embodiments, vibrational spectroscopy methods and apparatus are configured to measure levels of metabolites and proteins in blood. In many embodiments, mass spectrometry methods and apparatus are configured to measure one or more components of blood as described herein. In many embodiments, nuclear magnetic resonance (hereinafter "NMR") methods and apparatus can be configured to determine the presence of biomarkers of the one or more components of blood as described herein.

The spectroscopy may comprise one or more of molecular spectroscopy (infrared, near-infrared, UV, Raman, Surface enhanced Raman, resonance Raman, fluorescence, NMR, terahertz, far infrared, circular dichroism). Additional or alternative testing can be used such as a mechanical test (mechanical stiffness), or through a thermal property analysis (thermal gravimetric analysis TGA), for example, or rheology, for example.

Figure 6:
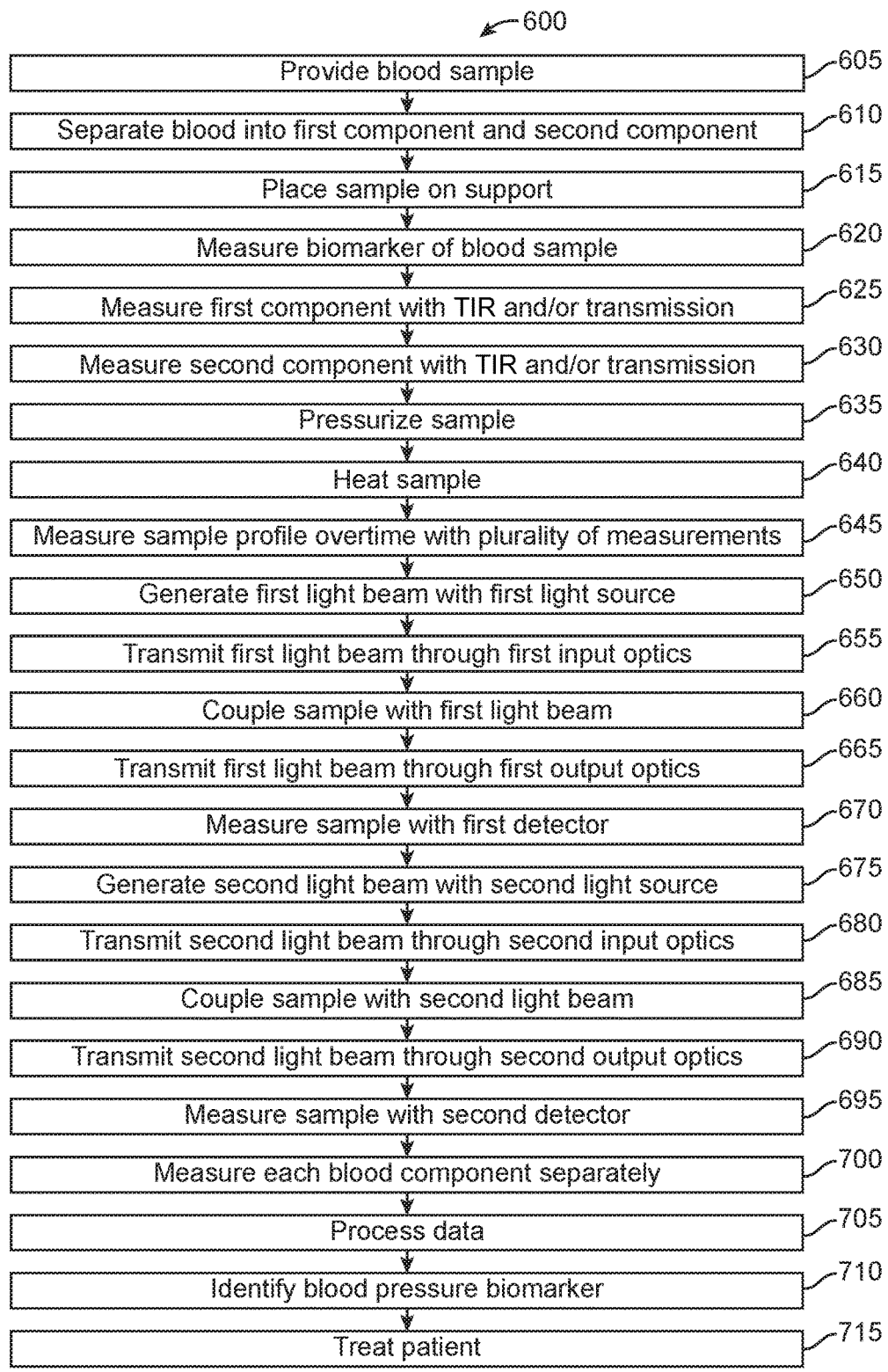
FIG. 6 shows a method of measuring blood pressure biomarkers, in accordance with embodiments.

FIG. 6 shows a method 600 of measuring biomarkers of blood such as blood pressure biomarkers, in accordance with embodiments.

At a step 605, a blood sample is provided. The blood sample may comprise a single drop of blood.

At a step 610, the blood is separated into a first component and a second component.

At a step 615, the sample is placed on the support.

At a step 620 a biomarker of the blood sample is measured.

At a step 625, the first component is measured with one or more of TIR or transmission spectroscopy.

At a step 630, the second component is measured with one or more of TIR or transmission spectroscopy.

At a step 635, the sample is pressurized.

At a step 640, the sample is heated.

At a step 645, the sample profile is measured over time with a plurality of measurements.

At a step 650, a first light beam is generated with a first light source. The first light beam may comprise a TIR light beam as described herein.

At a step 655, the first light beam is transmitted through first input optics.

At a step 660, the sample is coupled with the first light beam.

At a step 665, the first light beam is transmitted through the first output optics.

At a step 670, the sample is measured with the first detector.

At a step 675, a second light beam is generated with a second light source. The second light beam may comprise a transmission light beam for measuring a bulk thickness of the sample as described herein.

At a step 680, the second light beam is transmitted through second input optics.

At a step 685, the sample is coupled with the second light beam.

At a step 690, the second light beam is transmitted through the second output optics.

At a step 695, the sample is measured with the second detector.

At a step 700, each of the components of the sample is measured. For example each component can be measured with two measurement channels as described herein.

At a step 705, the data are processed.

At a step 710, a blood biomarker such as a blood pressure biomarker is identified. For example, the presence of the biomarker can be determined in order to establish the presence or absence of a biomarker.

At a step 715, the subject is treated.

The method 600 discloses a method of measuring blood pressure in accordance with embodiments. A person of ordinary skill in the art will recognize many variations and modifications based on the disclosure provided herein. For example, some steps may be added or removed. Some of the steps may comprise sub-steps, and many of the steps can be repeated.

The processor as described herein can be programmed with one or more instructions to perform one or more of the steps of the method 600 of measuring blood pressure of the subject, for example.

Therefore, the above steps are provided as an example of a method of measuring blood pressure of the subject in accordance with embodiments.

In many embodiments, a plurality of biomarkers is measured to identify the presence of high blood pressure of the subject. For example, a first biomarker can be measured and a second biomarker can be measured. In many embodiments, an amount of the first biomarker increases in response to the high blood pressure and an amount of the second biomarker decreases in response to the high blood pressure. Alternatively, amounts of both biomarkers can increase, or both amounts can decrease, for example. In many embodiments, a plurality of three or more biomarkers is measured, and an amount of a first at least one biomarker increases above a threshold amount to identify the high blood pressure and a second amount of a second at least one biomarker decreases below a threshold amount to identify the presence of the high blood pressure.

The methods and apparatus as described herein can be combined in one or more of many ways to measure one or more biomarkers of high blood pressure, and the embodiments disclosed herein provide examples, and a person of ordinary skill in the art will recognize many modifications based on the disclosure provided herein.

In many embodiments, one or more processors can be configured with machine learning software in order to correlate changes in the blood as exhibited in changes in the spectral patterns, quantitatively with high blood pressure. This software can use one or more the known tools of biostatistics, such as principle components analysis (PCA), principle components regression (PCR), partial least squares regression (PLS), classical least squares (CLS), multivariate curve resolution (MCR), neural networks, et cetera, for example.

In many embodiments, the biomarker for blood pressure comprises a positive marker for blood pressure such that the presence of the biomarker above a threshold amount indicates that the subject has high blood pressure. Alternatively, the biomarker for blood pressure comprises a negative biomarker for blood pressure such the presence of the negative biomarker above a threshold amount indicates that the subject does not have high blood pressure. In many embodiments, a plurality of biomarkers are measured in order to identify the presence (or absence) of high blood pressure.

The positive or negative biomarkers, and combinations thereof, can be identified in one or more of many ways as described herein, such as with PCA, PCR, MCR, CLS, PLS or neural networks, for example.

In many embodiments, the recent central aortic pressure encompasses at least about one day of blood pressure, such that the measure comprises an integral of subject blood pressure over at least about one day based on a single blood draw. In many embodiments, the recent central aortic pressure may comprise an integral of blood pressure over a period of time of about 3 to 4 months. The recent blood pressure may comprise one or more of a daily value or a 3-4 month period to determine long-term health and wellness and property therapeutic value of drug interventions, and durations in between for example. In many embodiments, the recent blood pressure comprises at least about a 24 hour duration in order to average out diurnal variations.

In many embodiments, the biomarker comprises one or more of the following:

Adenosine diphosphate, one or more transmembrane proteins (such as Band 3, Aquaporin 1, Glut1, ICAM-4, BCAM, Ankyrin, Band 4.1, Tropomyosin, Actin, or glycophorin), one or more proteins of the membrane skeleton (such as spectrin), one or more lipids of the red blood cell membrane, a relative ratio of the one or more lipids of the red blood cell membrane, or biomaterial deposited on the surface of the red blood cell membrane. Lipids in the RBC membrane include Phosphatidylcholine (PC); Sphingomyelin (SM) in the outer monolayer, and Phosphatidylethanolamine (PE), Phosphoinositol (PI) (small amounts) and Phosphatidylserine (PS) in the inner membrane. Approximately half the mass of the RBC membrane is proteins and half is phopholipids. The ratio of protein to lipid may change with high blood pressure, or the relative ratio of various lipids may vary. For example the ratio of Phosphatidylcholine to Sphingomyelin might be 60:40 in a healthy individual, but may change to 50:50 in high blood pressure. Or the ratio of total lipid to total protein may change from 50:50 in a healthy individual to 60:40 in high blood pressure.

The biomarker may comprise one or more of specific changes to the secondary structure of the transmembrane proteins, the proteins of the membrane skeleton of the red blood cell, or changes to the composition and relative ratios of membrane lipids of the red blood cell membrane, and combinations thereof, for example. Alternatively or in combination, the biomarker may comprise biomaterial coated on the surface of the red blood cells that has been deposited by contact with biomaterials inside the vasculature, for example deposited in response to abrasive contact. In many embodiments, the biomarker comprises one or more of a change to the protein composition of the red blood cell membrane, a change to the structure of the red blood cell membrane, a change to the structure or composition of the lipids of the red blood cell membrane, an endogenous biomaterial deposited onto the outside of the red blood cell through contact during flow of the cells through the vessels, or a foreign biomaterial deposited onto the outside of the red blood cell through contact during flow of the cells through the vessels, for example.

Figure 7:
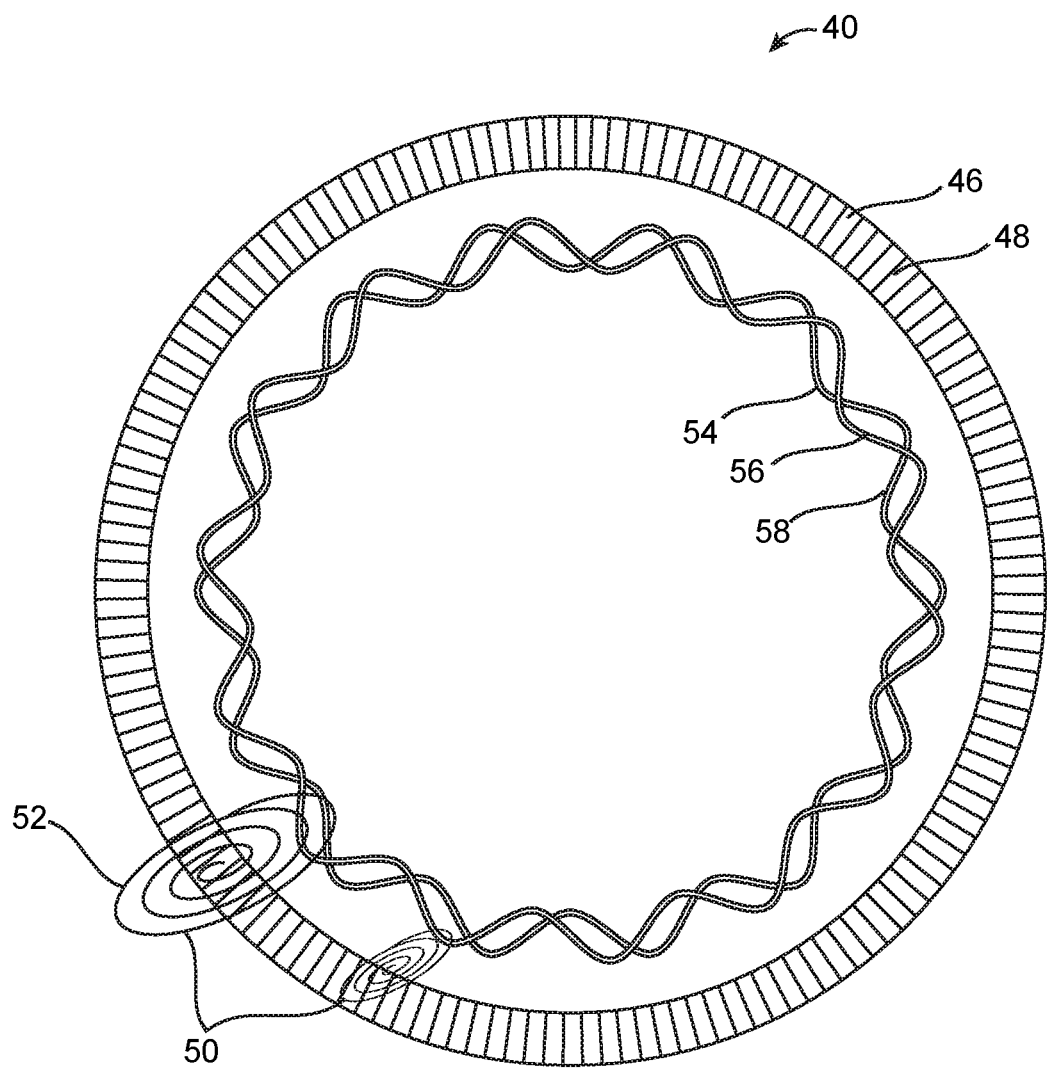
FIG. 7 shows a substantially circular cross-section through a red blood cell, in accordance with embodiments.

FIG. 7 shows a cross section of a red blood cell 40 in accordance with embodiments. The circular cross section shows structures of the red blood cell membrane 46, membrane proteins 50, and structural proteins 54 within the red blood cell. The circular cross sectional view shows the lipid bi-layer 48 of the red blood cell membrane, which may comprise a phospholipid bi-layer for example, cholesterol, and phosphatidyl choline, for example. The ratio of components of the lipid bi-layer can be measured in accordance with embodiments. The membrane protein 50 may comprise one or more of many known membrane proteins, such as trans-membrane proteins 52, for example. The membrane protein may comprise one or more of Band 3, Ankyrin, CD47, Rh, or Glycophorin, for example. For example, the red blood cell membrane may comprise trans-membrane protein such as Ankyrin extending through the membrane in order to transmit ions for example. The red blood cell membrane may comprise interior protein such as spectrin protein, for example a spectrin network 58 extending substantially along an interior of the cell membrane and interior to the cell wall.

In many embodiments, the red blood cell membrane corresponds to a fluid mosaic model of biological membranes, and membranes in addition or alternative to the red blood cell membrane can be measured. The membrane may comprise membrane proteins which are mobile within the phospholipid and cholesterol layer. The spectrin network of the membrane skeleton 56 provides strength to the red blood cell membrane by interacting with the other proteins of the membrane as described herein.

In accordance with embodiments, changes in the red blood cell membrane and structures associated with the red blood cell membrane can be measured. For example, lipids can be measured and changes in lipids, lipid ratios and changes in lipid ratios, proteins can be measured, protein ratios can be measured and protein to lipid ratios can be measured.

The measurement in the analysis of the red blood cell membrane can be performed in one or more many ways, for example, with principal component analysis (PCA).

Figure 8:
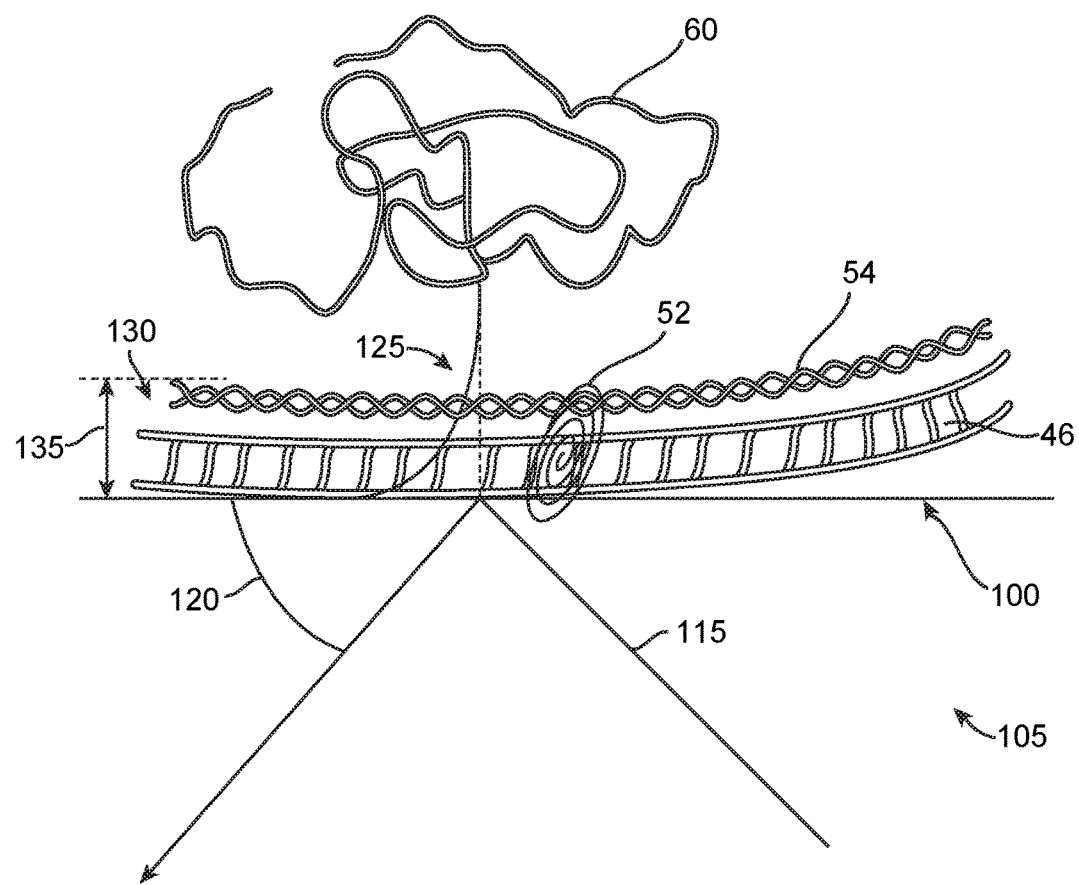
FIG. 8 shows measurement of a red blood cell membrane and related structures, in accordance with embodiments.

FIG. 8 shows an enlarged view of the red blood cell membrane 46 placed on a support structure 105 for measurement in accordance with embodiments. The support comprises an optically transmissive material as disclosed herein and the evanescent field 125, an evanescent vector extending at least partially beyond an upper or measurement surface 100 of the support on which the red blood cell membrane reside. A light wave is infinite on the upper surface of the support at an incidence angle 120 of theta. The measurement light 115 comprises a wavelength lambda. The depth 135 of the evanescent field comprises a zone of sensitivity 130. The zone of sensitivity can be adjusted based on combinations of one or more of the incidence angle Θ (theta) and the wavelength of light λ (lambda), in order to limit the depth of the zone of sensitivity of the measurement. The limitation of the measurement depth provides measurement of the cell membrane on the surface, such as the red blood cell membrane and corresponding structures such as the trans-membrane proteins 52 and the structural proteins 54, and inhibits measurement of deeper structures such as hemoglobin 60, for example. The measured structures of the membrane can be structures of the intact cell, and may comprise one or more of the trans-membrane protein Ankyrin and the structural protein Spectrin, for example.

The red blood cell may comprise an intact red blood cell as described herein. The zone of sensitivity can inhibit measurement of hemoglobin with a zone of sensitivity corresponding substantially to the red blood cell membrane, the lipid bi-layer of the red blood cell membrane, trans-membrane proteins of the red blood cell membrane, and structural support proteins of the red blood cell membranes, such as, spectrin for example. In many embodiments hemoglobin is positioned within the intact red blood cell at locations away from the red blood cell membrane such that the zone of sensitivity does not extend substantially into a hemoglobin molecule and, for example, does not extend across a hemoglobin molecule within the red blood cell membrane. These embodiments can provide specificity to the measurement and localization to the red blood cell membrane.

In accordance with embodiments described herein, ratios of components of the red blood cell or other membranes of another cell can be measured. For example, the ratio of phosphatidyl choline to cholesterol can be measured. The ratios of phospholipids to other components can be measured such as the ratio of one or more lipid components to a ratio of one or more protein components.

The components of the red blood cell membrane can be measured in one or more of many ways, and reference is made to spectroscopy merely by way of example in accordance with embodiments.

Alternatively or in combination, rheology can be used to measure the components of the red blood cell membrane. The rheology measurement apparatus may comprise one or more capillary tubes having a diameter size to inhibit flow and limit flow and provide at least some resistance to blood flow, for example. The rheology of the plurality of red blood cells measured may correspond to structural aspects of the surface exterior, which can be affected by one or more substances on the surface of the red blood cells, for example.

The rheology components can be measured with a transform function and transfer function. For example, the flow characteristics of the red blood cells of the blood sample through capillary tubes can be measured and the impedance profiles determined for plurality of frequencies in order to determine a transform function spectra. The impedance of the blood flow through the one or more capillary tubes is measured at a plurality of frequencies in order to provide a spectrum. The mechanical spectral data can be combined with optical spectral data as described herein. Alternatively, the mechanical spectral data can be used to determine the presence of one or more biomarkers.

The rheology embodiments are well suited for combination with the optical embodiments. For example, the aggregation of red blood cells can affect the measured flow parameters of the blood, and the aggregation of the red blood cells can also be related to one or more surface components of the red blood cell membrane as described herein, for example.

In many embodiments the analysis comprises a principal component analysis (PCA), comprising the plurality of dimensions and the dimensions may comprise orthogonal eigenvectors for example. A person of ordinary skill in the art will have at least some familiarity with PCA, and can determine the presence or absence of biomarkers from a blood sample with PCA, for example.

Figure 9:
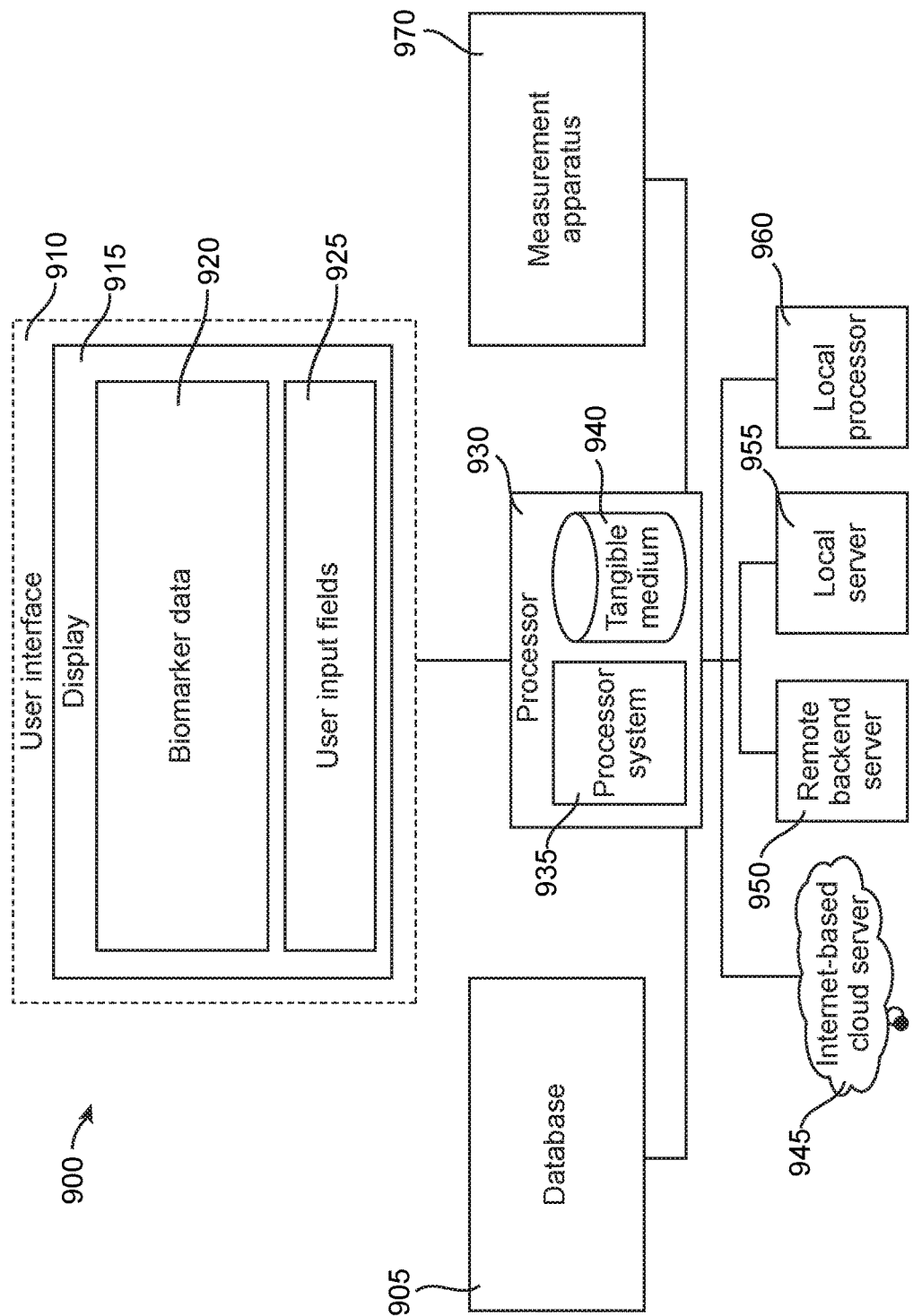
FIG. 9 shows an apparatus comprising a database and a user interface to determine identify markers of red blood cells related to health, in accordance with embodiments.

FIG. 9 shows an apparatus 900 comprising a database 905 and a user interface 910 to determine identify markers of red blood cells related to health in accordance with embodiments. The apparatus 900 may optionally comprise one or more components of the measurement apparatus 970 as disclosed herein, such apparatus 500, for example. The user interface comprises a display 915 connected to a processor 930 such that the user can view the biomarker data 920 on the display. The user interface also comprises one or more user input fields 925. The processor may comprise a processor system 935 and can store data of the database for the user to see information of the database on the display. The processor comprises a tangible medium 940 storing instructions of the database, such that the user can see the information on the display. The tangible medium may comprise a computer readable medium having one or more of many known forms such as random access memory (RAM), read only memory (ROM), compact disc CD-ROM, flash RAM. The processor may comprise one or more of a plurality of Internet based cloud servers 945, a remote back end server 950, or a local server 955, or a local processor 960 for example. The display may comprise a display of a hand held processor such as a smart phone in communication with a server, for example. Each of the components of the apparatus 900 can be connected in one or more of many ways as will be apparent to a person of ordinary skill in the art, and each of the components as shown can be connected to another component, either directly or indirectly through other components and communication pathways as disclosed herein.

The measurement apparatus as described herein can be combined with the database and user interface in many ways. In many embodiments, data from the measurement apparatus is shown on the display. The data shown on the display may comprise data of the amplified red blood cell measurement signal as described herein. In many embodiments, output of the processor system, can be shown on the display, in accordance with steps of one or more methods as described herein, and the one or more processors may comprise instructions to perform the one or more method steps and output the data on the display. In many embodiments, the data output to the user interface comprises cell membrane amplification data as described herein, such as data of a plurality of cell membranes shown on the display. The data of the plurality of cell membranes may comprise evanescent wave data of a plurality of intact red blood cell membranes, for example. In many embodiments, amplified data comprises amplified cell membrane data of a plurality of washed cells, such as gravimetrically separated washed red blood cells as described herein. The data shown on the display to the user may comprise one or more biomarkers of health from the gravimetrically separated and washed membranes of intact red blood cells, for example. The one or more processors as described herein can be configured to with instructions stored on a tangible medium such as a computer readable medium to provide the data on the display.

FIG. 10 shows light 115 entering germanium optical structure 110 (index of refraction n=4) at an incident angle 145 of 80 degrees. This incident angle results in total internal reflection and a very shallow 1/e penetration depth 135 of the resulting evanescent wave 140 into the sample. The sample can comprise red blood cells 40, as shown. The ends of the germanium can be anti-reflection (AR) coated. The germanium optical structure may comprise one or more inclined prism surfaces as described herein, and may comprise waveguide as described herein, for example.

Table 1 shows penetration depths for various angles of incidence and wavelengths in different sampler surfaces (diamond, silicon, and germanium), in accordance with embodiments.

TABLE 1

Penetration Depths
Table 1. Penetration Depths

| sampler surface | angle of incidence (degrees) | depth of penetration (microns) | sample index n2 | window index n1 | wavelength (microns) |
|---|---|---|---|---|---|
| diamond | 35 | 0.958 | 1.33 | 2.39 | 2 |
| diamond | 45 | 0.305 | 1.33 | 2.39 | 2 |
| diamond | 75 | 0.169 | 1.33 | 2.39 | 2 |
| diamond | 35 | 3.354 | 1.33 | 2.39 | 7 |
| diamond | 45 | 1.068 | 1.33 | 2.39 | 7 |
| diamond | 75 | 0.590 | 1.33 | 2.39 | 7 |
| diamond | 35 | 4.792 | 1.33 | 2.39 | 10 |
| diamond | 45 | 1.526 | 1.33 | 2.39 | 10 |
| diamond | 75 | 0.843 | 1.33 | 2.39 | 10 |
| silicon | 35 | 0.221 | 1.33 | 3.42 | 2 |
| silicon | 45 | 0.158 | 1.33 | 3.42 | 2 |
| silicon | 75 | 0.105 | 1.33 | 3.42 | 2 |
| silicon | 35 | 0.773 | 1.33 | 3.42 | 7 |
| silicon | 45 | 0.552 | 1.33 | 3.42 | 7 |
| silicon | 75 | 0.368 | 1.33 | 3.42 | 7 |
| germanium | 35 | 0.169 | 1.33 | 4.02 | 2 |
| germanium | 45 | 0.127 | 1.33 | 4.02 | 2 |
| germanium | 75 | 0.087 | 1.33 | 4.02 | 2 |
| germanium | 35 | 0.591 | 1.33 | 4.02 | 7 |
| germanium | 45 | 0.443 | 1.33 | 4.02 | 7 |
| germanium | 75 | 0.305 | 1.33 | 4.02 | 7 |
| germanium | 35 | 0.845 | 1.33 | 4.02 | 10 |
| germanium | 45 | 0.634 | 1.33 | 4.02 | 10 |
| germanium | 75 | 0.436 | 1.33 | 4.02 | 10 |

Figure 11A:
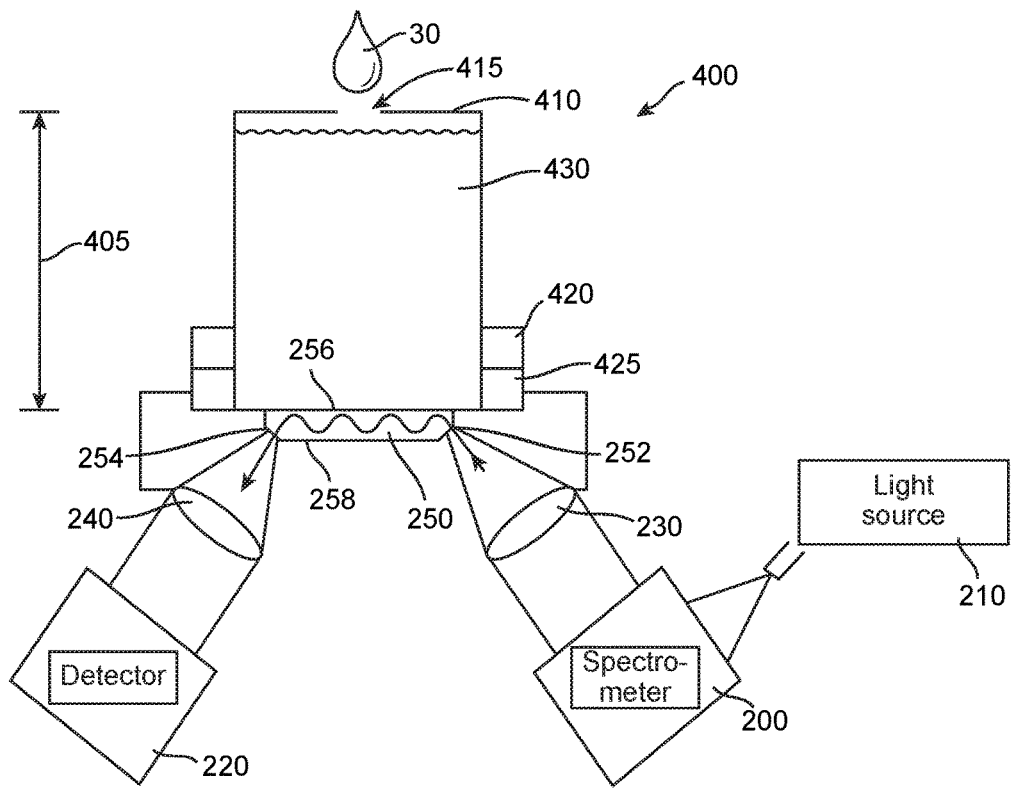
FIG. 11A shows a sample gravimetric washing container and spectrometer to measure a blood sample, in accordance with embodiments.

FIG. 11A shows a sample gravimetric washing container or holder 400 and spectrometer 200 to measure a blood sample 30. In many embodiments, the container is coupled to the spectroscopic measurement apparatus as disclosed herein. The internally reflective structure may comprise a waveguide 250 optically coupled to the cells such as red blood cells 40 placed in the container. The container comprises a vertically extending length 405 to provide gravimetric separation. A cover or lid 410 extends over an upper portion of the container. The cover comprises an opening 415 formed in the cover. A capillary tube may extend to the opening in the cover.

In many embodiments the measurement apparatus comprises a support fixed in relation to the spectrometer optics such that the container can be removed. The support may comprise a lower support 425 fixed in relation to the optics of the spectrometer such that the container can be placed on the lower support. The container may comprise an upper support 420 affixed to the container such that the container can be removed. The fixed lower support can be sized to receive a portion of the container in order to engage the upper support. The measurement apparatus comprises input coupling optics 230 such as a lens to couple the light source 210 of the spectrometer to the waveguide structure of the container, and output coupling optics 240 such as lens to couple the output of the waveguide structure to photodetectors 220.

In many embodiments, the upper support, the lower support and the coupling optics are arranged to couple the waveguide to the coupling optics when the upper support rests on the lower support. In many embodiments, the upper support comprises a lower flange or rim of the container sized and shaped to be received with the lower support and align the waveguide structure with the coupling optics when received in the lower support.

Gravimetric separation can be performed in a solution 430. The solution can be isotonic compared to blood, or can be hypertonic or hypotonic compared to blood, and combinations thereof. Hypertonic or hypotonic solution can result in conformational changes in red blood cells which may be useful for subsequent analysis. The solution can comprise saline. The solution can comprise components with known spectral bands for spectroscopic calibration, such as for example ethanol or methanol, and each spectra can be determined in response to the known spectral bands, for example. A container, of solution can be positioned on top of a prism or other spectrometer sampling element, for example as shown in FIG. 11A. The container can be shaped in one or more of many ways and may comprise a cylindrical column, for example. The container comprises a vertically extending length sufficient to allow gravimetric separation of the red blood cells from other components of the red blood cell sample such as the serum.

In many embodiments, the container column is placed on top of a waveguide structure such as prism, for example. The container may comprise a lower membrane having a thickness less than the 1/e depth of the evanescent wave in order to measure the blood sample through the membrane A thin optically transmissive material can be located on the upper surface of the waveguide, in which the thin material comprises a thickness less than the 1/e penetration depth of the evanescent wave, for example.

The waveguide structure can be dimensioned in one or more of many ways as disclosed herein. In many embodiments the waveguide comprises a first end 252 to receive light energy and a second end 254 to transmit light energy. The wave guide may comprise an upper surface 256 on an upper side oriented toward the sample and a lower surface 258 on a lower side oriented away from the sample. The waveguide may comprise a thickness extending between the upper surface and the lower surface. In many embodiments the waveguide comprises a length extending in a direction of propagation from the first end to the second end. The waveguide may comprise a width transverse to the length. In many embodiments, the waveguide comprises a width greater than the thickness and a length greater than the width in order to provide a plurality of internal reflections of the measurement light energy from the upper surface of the waveguide in order to amplify the optical signal transmitted from the second end of the waveguide.

The ends of the waveguide can be configured in one or more of many ways and may comprise surfaces extending perpendicular to a long dimension of the waveguide, or inclined at an angle so as to comprise prismatic surfaces. In many embodiments, the waveguide comprises a prism, for example a dove prism as described herein.

Alternatively or in combination, the removable container 400 may comprise the waveguide structure 250. The waveguide structure can be removable with the container and located on the lower end of the container. The container can be removed or placed with the upper lid with comprising an upper hole or capillary for introducing sample into the container. A sample comprising red blood cells can be introduced to the container, and the relatively heavier red blood cells can be separated gravimetrically and settle onto the sampling surface either before or after the container has been placed on the support.

In many embodiments, the red blood cells can be washed by the solution during the gravimetric separation, such that potential contaminants can be removed from the measurement.

Figure 11B:
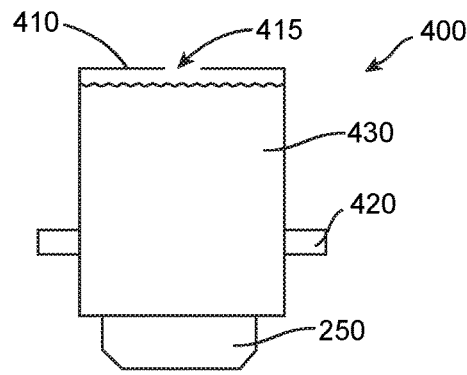
FIG. 11B shows a container as in FIG. 11A removed from the spectrometer.

FIG. 11B shows a container 400 as in FIG. 11A removed from the spectrometer. In many embodiments, the container comprises a removable container, such that the container comprises a single use consumable item and the spectrometer components can be reused. In many embodiments, the apparatus comprises a fixed support structure that engages a removable support 420 affixed to the container. The container can be accurately coupled to the spectrometer with a support structure such as a flange, collar, or other support on the container itself. The spectrometer and associated light source and detector can be used to take measurements with the waveguide 250 on the lower end of the container.

In many embodiments the lower support is fixed in relation to the optics of the spectrometer, such that placement of the container comprising the waveguide can be aligned with the measurement optics when placed in order to provide accurate spectroscopic measurements. One or more of the upper support or the lower support can be sized and shaped in order to position the waveguide with a position and orientation for measurement of the cells on the lower surface of the container, for example.

Additional components can also be added to the container to alter the sample if helpful. For example, gluteraldehyde can be added to the column to alter red blood cell membrane structure.

In many embodiments, a plurality of gravimetric separation containers is provided, in which each container of the plurality comprises a removable single use consumable container.

In many embodiments, spectra can be measured from the sample and statistical analysis methods can be used to generate a plurality of factors. The plurality of factors may comprise a plurality of functions upon which the data can be projected in order to determine the amount, or concentration, of each function in the sample. The factors can be orthogonal or non-orthogonal, for example. The analysis can comprise one or more of principle components analysis (PCA), principle components regression (PCR), classical least squares (CLS), multivariate curve resolution (MCR), partial least squares regression (PLS), neural networks, or other biostatistical or chemometric approaches, for example. In many embodiments, the factors are orthogonal to each other. Alternatively, at least some of the factors may comprise non-orthogonal factors. One or more relevant factors can be identified, and the red blood cell status or history can be determined in response to the one or more relevant factors. In many embodiments, the history of the red blood cells comprises a control of the red blood cells of the subject, for example a control of a condition such as high blood pressure of the subject. The one or more relevant factors may comprise one or more statistically relevant factors, for example.

In many embodiments, a plurality of spectral bands comprise peaks related to structure of the cell such as protein structure of the red blood cell. The Amide I band of frequencies comprising the Amide I peak may correspond to alpha helix protein structures of the proteins of the red blood cell membrane. The Amide II band of frequencies comprising the Amide II peak may correspond to beta-sheet protein structures of the cell membrane. The band of frequencies comprising the Amide III band may correspond to disordered protein structures of the cell membrane. The determination of factors corresponding to these spectral bands and the shifts of peaks and intensities of these spectral bands in response to the measure spectra can be used to determine the one or more biomarkers of the cellular membrane such as the red blood cell membrane.

In many embodiments, deformation of the red blood cell membrane results in measurable spectroscopic changes to the red blood cell membrane that can be measured as described herein. The measurable changes may comprise shifts in the spectral peaks as disclosed herein. The spectroscopic changes to the red blood cell membrane can be substantially instantaneous, for example upon deformation of the red blood cell membrane. Alternatively, the spectroscopic changes to the red blood cell membrane may comprise changes occurring over the history of the red blood cell, for example over a long term three month history corresponding to the 90 to 120 day functional lifetime of the red blood cell.

In many embodiments the factors can be used to determine the history of the red blood cell, and can be used to determine the long term control of a condition such as hypertension, for example. The long term control may comprise a conformational change to the red blood cell membrane that can be determined with at least one factor as disclosed herein, for example with a relationship among factors as disclosed herein.

In many embodiments, the biomarker amplifies an optical spectral signal. The biomarker may comprise a change to cell membrane, such as a conformational change to a protein of a red blood cell membrane or a ratio of components of the red blood cell membrane as disclosed herein, for example. As the red blood cells comprise a long dimension that can extend along the measurement surface and optically couple the red blood cell membrane to the evanescent wave measurement surface, the measured signal can be amplified substantially. In many embodiments, a substance related to the health status of the subject may not itself be detectable with the spectral measurements. The measurement of the red blood cell membrane can provide, however, an optical spectral signal to determine the presence of the substance. For example, spectral changes of the red blood cell membrane provided with aspirin as disclosed herein can be used to identify a response of the red blood cell membrane to aspirin, even though the presence of aspirin itself may not be detectable spectroscopically in some embodiments. The optical waveguide can be configured to provide a plurality of reflections from the evanescent wave measurement surface in order to provide an increased amplification of the measured evanescent wave signal.

Figure 11C:
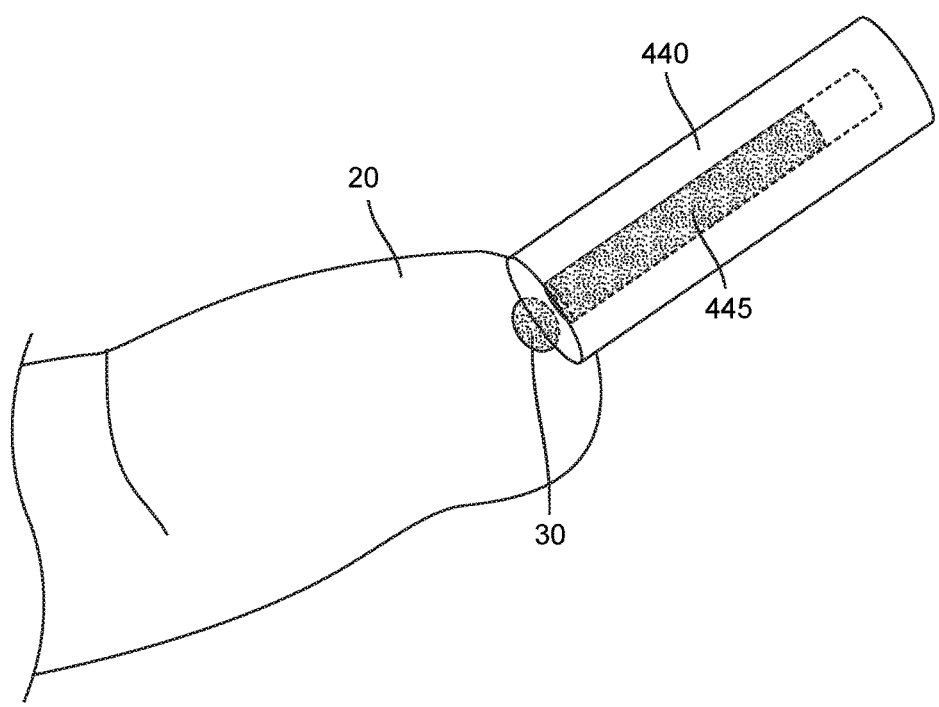
FIG. 11C shows a draw tube, in accordance with embodiments.

FIG. 11C shows a tube 440 to draw a sample. The draw tube can be used to draw a blood sample 30, such as a sample from a pool of blood on an external surface such as an external surface of a finger 20. In many embodiments, the draw tube comprises a permeable membrane having pores sized to wash the sample. Alternatively, the draw tube may comprise an impermeable membrane for placement of the sample in a container as described herein.

Figure 11D:
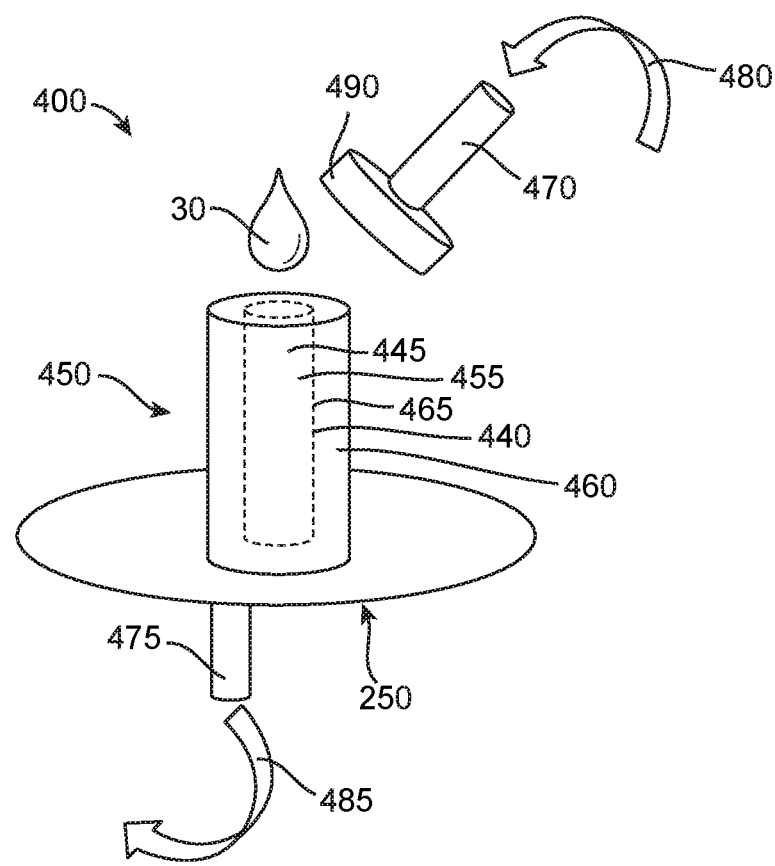
FIG. 11D shows sample delivery and cell washing, in accordance with embodiments.

FIG. 11D shows sample delivery and cell washing with a removable sample holder 400 as described herein. The sample holder 400 may comprise a container 450 coupled to an inlet tube 470 and an outlet tube 475. The inlet tube can provide a rinse solution 480 and the outlet tube can pass rinsate 485 from the sample container. The sample container may comprise an inner portion 455 and an outer portion 460 with the permeable membrane 465 extending therebetween, in order to provide cross-flow filtration, for example. The inlet tube can be connected to the inner portion of the sample container and the outlet tube can be connected to the outer portion of the sample container. An attenuated total reflection (ATR) waveguide crystal 250 can be located on a lower end of the sample container. The cells of the sample 30 can be retained in the draw tube and deposited onto the ATR crystal for measurement as described herein. The rinsate column has the advantage of removing non-cellular material from the measured sample, such as serum and potential lysate.

The sample draw tube 440 as in FIG. 11C comprising the semipermeable membrane 465 can be used to collect a blood sample 30, and the draw tube comprising the permeable membrane can be placed in an annular container 450 comprising a column of fluid. Alternatively, a drop of blood can be placed on an upper end of the draw tube in order to receive the blood sample with the tube. The permeable membrane may comprise an approximate pore size of about 5 um in order to inhibit passage of cells through the pores and to allow passage of water and molecules, for example, in order to wash the sample.

A cover 490 can be placed over the annular container in order to wash the sample. The cover may comprise an inlet tube extending from the cover. The cover may comprise an opening formed therein coupled to a lumen 445 of the tube 440 placed into the container 450, to pass fluid from the tube through the cover and into the draw tube. An outlet can be coupled to an outer annular portion of the annular container defined by the draw tube. The draw tube can be placed within the annular container such that the lumen of the draw tube defines a first inner portion of the annular container within the draw tube and a second outer annular portion of the annular container outside the draw tube.

The outlet tube can be connected to a lower portion of the outer portion of the container as shown. Alternatively, the outlet tube can be coupled to an upper portion of the sample container, and may be integrated with the cover, for example, such that both the inlet tube and the outlet tube extend from the cover.

The ATR waveguide crystal as described herein can be located on a lower end of the annular container, and coupled to spectrometer optics, such that the sample container comprises a removable sample container among a plurality of sample containers as described herein. The waveguide can be located on a lower end of the draw tube, for example.

Figure 12:
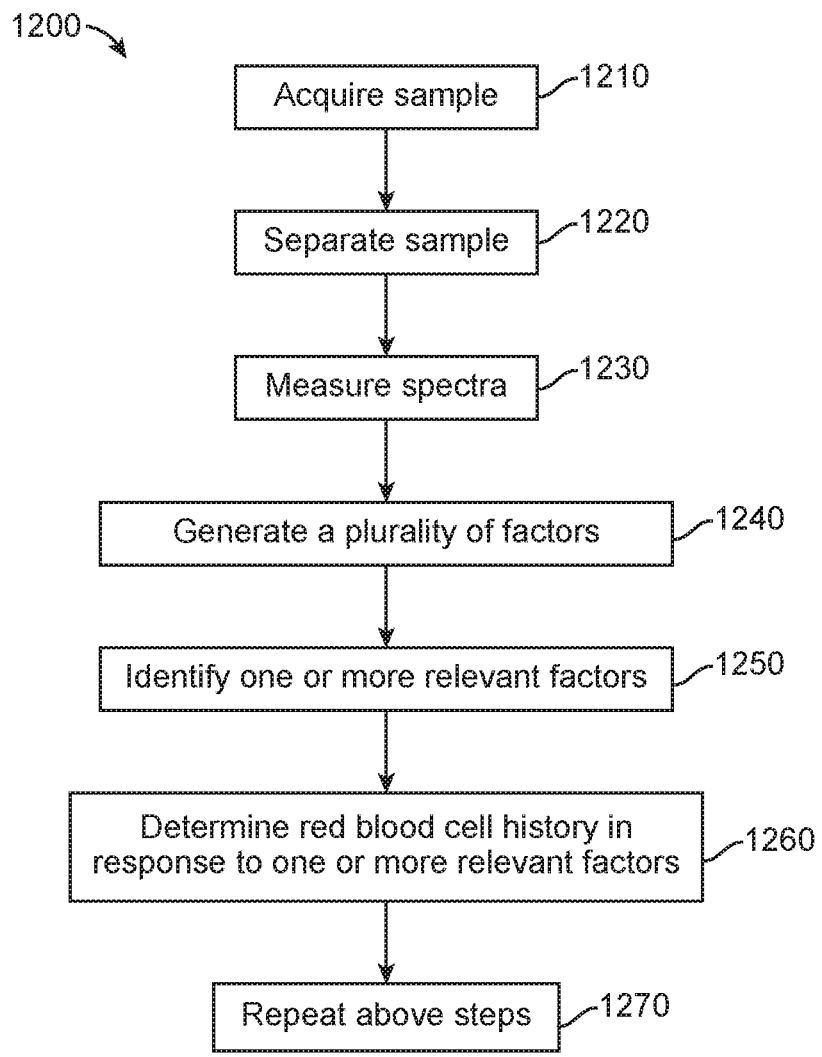
FIG. 12 shows a method of analyzing a sample, in accordance with embodiments.

The sample holder 400 comprising the container has the following advantages:
Washes the serum and potential lysate from the cell membranes
 Packs cells onto ATR crystal
 Disposable
The sample container can be used with one or more of the following steps:
 Wash Cycle
 Washes serum and potential lysed material into rinsate column;
 Drain Cycle
 Drains a the rinsate column and in addition drains a majority of the membrane straw leaving a layer of cells on ATR crystal; and
 Measure Cycle.
 Begin spectroscopic measurement when sufficient cell membrane signal exists FIG. 12 shows a method 1200 of analyzing a sample. At a step 1210, the sample is acquired as described herein. At a step 1220, the acquired sample is separated as described herein, for example with gravimetric separation and washing. At a step 1230, spectra are measured from the sample and statistical analysis methods can be used to determine the history of the cell such as the red blood cell. The analysis methods may comprise one or more of principle components analysis (PCA), principle components regression (PCR), multivariate curve resolution (MCR), classical least squares (CLS), partial least squares regression (PLS), neural networks, or other biostatistical or chemometric approaches, for example. At a step 1240, a plurality of factors is generated. The factors can be orthogonal to each other, for example. At a step 1250, one or more relevant factors is identified. At a step 1260 the red blood cell history is determined in response to the one or more relevant factors. At a step 1270, the above steps are repeated.

FIG. 12 shows a method of analyzing a sample in accordance with embodiments. A person of ordinary skill in the art will recognize many adaptations and variations in accordance with the embodiments disclosed herein. For example one or more steps can be deleted. Steps can be added, and some steps can be repeated. At least some of the steps may comprise sub-steps.

The method 1200 can be embodied with instructions of a processor on a tangible medium. The processor may comprise one or more a computer, a cloud computer, a computer network, a digital processor, a digital signal processor, gate array logic, field programmable gate array, programmable array logic. The tangible medium comprises may comprise a storage structure to store instructions of the processor, for example a computer readable memory such as flash memory, random access memory or a hard disk drive.

The methods and apparatus disclosed herein can be configured in one or more of many ways to measure vibrational spectroscopy of the sample, such as infrared (IR) spectroscopy, near infrared spectroscopy, visible spectroscopy, Raman spectroscopy, nuclear magnetic resonance (NMR) spectroscopy, total internal reflection (TIR) spectroscopy, TIR-IR spectroscopy, transmission spectroscopy, transmission IR spectroscopy, or transmission near-IR spectroscopy.

The methods and apparatus disclosed herein can be configured to determine spectral changes in a blood sample in response to one or more of drying of the blood sample, washing of the blood sample, hyper-molality of the blood sample, hypo-molality of the blood sample, temperature of the blood sample, heating of the blood sample, cooling of the blood sample, pressure of the blood sample, pressurization of the blood sample, and depressurization of the blood sample.

For example, the methods and apparatus described herein can be configured to measure spectroscopic data of red blood cells over a time period of a drying process. The red blood cells may be purified and washed, e.g., resuspended to 20% hematocrit in phosphate buffered saline, then subjected to a gradual drying process, and the sample may be measured spectroscopically as described herein at regular time intervals. Such a measurement can provide a study of how the chemical composition, protein structure and/or conformation of the red blood cell membrane changes over a drying process. Work in relation embodiments suggests that the methods and apparatus as described herein may be well-suited for the measurement of dried blood samples. Without being bound by any particular theory, the drying of red blood cells can provide some enhancement in spectroscopic measurements. For example, since water is known to interfere with infrared measurements, the removal of water from the sample may improve the spectral signal of the sample of interest. Alternatively or in combination, the removal of water from the sample may cause the sample region of interest, e.g., red blood cell membranes, to adsorb on the measurement surface, resulting in an improvement of the spectral signal of interest. Removal of at least some water from the blood samples may further inhibit lysing of the red blood cells, such that the red blood cell membranes remain substantially intact during measurement. Accordingly, the methods and apparatus disclosed herein may be configured to identify blood pressure of blood samples with at least some water removed from the blood sample, in order to improve the spectral signal of the red blood cell membranes. For example, the blood samples with about 50% of the water of the blood sample removed may be measured.

The methods and apparatus as described herein may also be configured to measure spectroscopic data of blood samples at different osmolalities, which may cause red blood cells to shrivel, expand, lyse, or otherwise undergo conformational changes. A plurality of spectra may be obtained from the blood sample, each spectra corresponding to a different osmolality.

The processor as described herein can be configured to identify a condition of the patient, such as one or more of high blood pressure or malaria, for example. The processor system can be configured to analyze the sample as described herein, for example with one or more of a least squares fit or a classic least squares fit, for example. Spectral shapes can be associated with blood pressure, such as mean arterial blood pressure, systolic blood pressure, diastolic blood pressure, or pulse pressure, for example. The processor may comprise instructions to identify high blood pressure of the patient in response to one or more spectral signatures as described herein, for example by determining a plurality of spectral factors as described herein The methods and apparatus disclosed herein can be used to identify a condition of a patient in response to spectra of a blood sample of the patient. The thus-identified condition may be used to determine an appropriate course of treatment for the patient, such as to identify a drug to administer to the patient or to determine the amount of said drug to administer to the patient. For example, the processor of the apparatus may comprise instructions to determine an amount of drug to provide to the patient in response to spectral data of the patient's blood sample. One or more clinical trials may be conducted to validate the identification of the course of treatment using spectral measurements of a patient's blood sample. For example, the amount of drug for administration to the patient, determined using the measurement of blood spectral data, may be validated with one or more clinical trials.

The methods and apparatus disclosed herein may be suitable for incorporation with clinical trials. For example, a method of performing a clinical trial to evaluate a safety and/or efficacy of a treatment with a device and/or drug may comprise using the measurement apparatus as described herein to measure blood samples of patients.

The methods and apparatus can be configured to provide a differential measurement of the sample, with first spectra measured without the sample to calibrate the instrument and second spectra measured with the sample. The calibration measurements can be obtained with the sample holder placed in the spectrometer and without the sample.

The sample can be measured without over fitting the data, for example.

While many computation methods can be used as described herein, classical least squares can be used to fit bands and functional groups and provide functional group analysis, for example. Alternatively or in combination, partial least squares fitting can be used. Known factors such as one or more of water or water vapor can be added to the sample a priori, for example. Augmented classical least squares can be used to analyze the spectral data.

The methods and apparatus as described herein can be configured with instructions to provide augmentation of the calibration space. While the calibration space augmentation can be performed in one or more of many ways with the factors and functions methods as described herein, the calibration space augmentation may comprise one or more of an augmented classical least squares of the calibration space data, an augmented partial least square of the calibration space data, or an multivariate curve resolution of the calibration space data. An iterative fit can be performed to linearly independent spectral data sets, for example. A spectral signature can be developed for one or more of the calibration space data or the blood sample data, for example. The spectral signature of the calibration space data can be used for later analysis of the blood sample as described herein, for example with one or more of partial least squares, augmented classical least squares, multivariate curve resolution, or other chemometric approach as described herein, for example.

Figure 22:
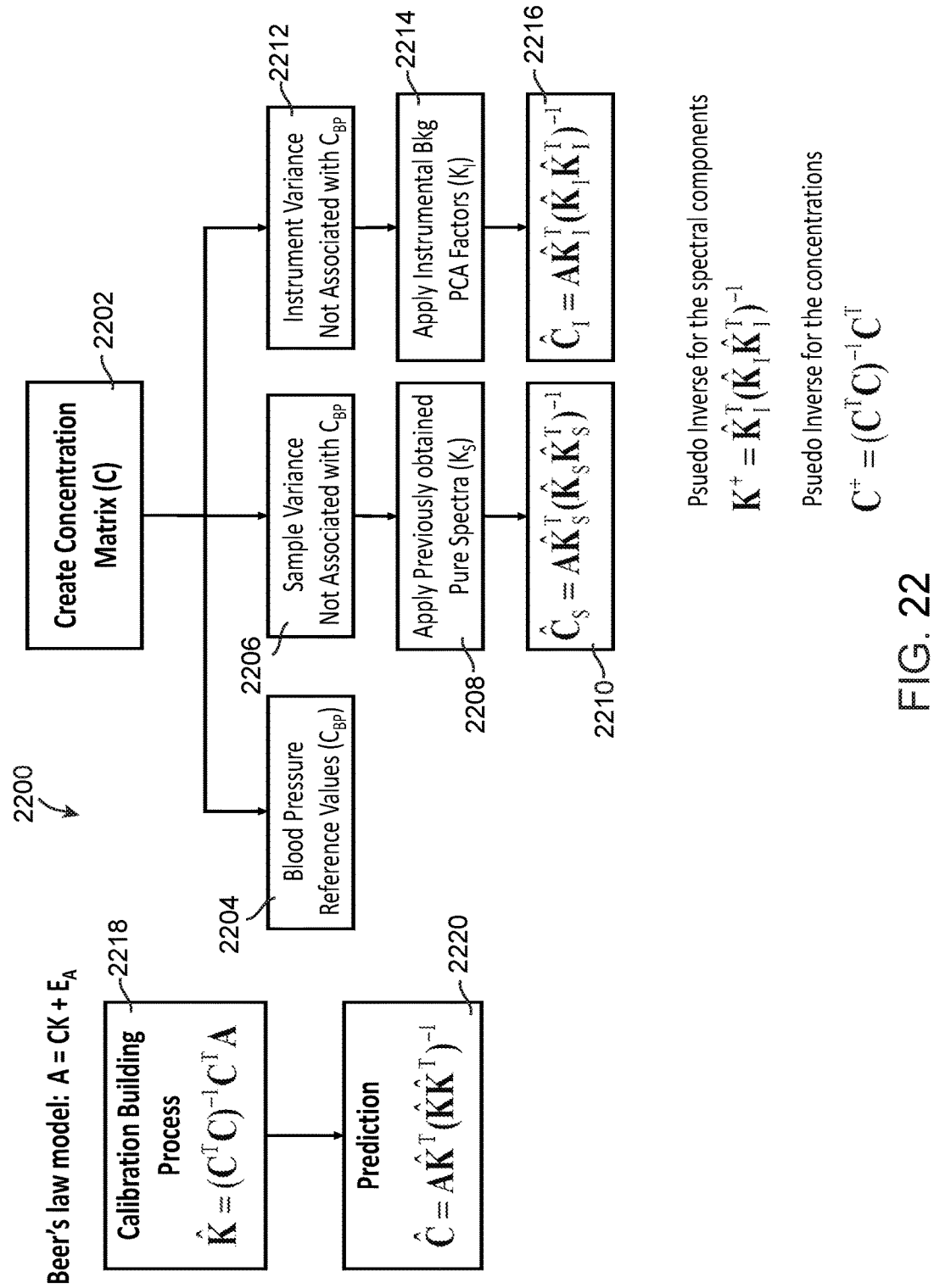
FIG. 22 shows a method of spectral data analysis suitable for incorporation with embodiments.

FIG. 22 shows a method 2200 of spectral data analysis suitable for incorporation with embodiments. A variant of Classical Least Squares (CLS) may be used to build calibration models and predict blood pressure values based on red blood cell spectra. This CLS variant has been referred to as Augmented CLS and can often be performed during the prediction process. CLS assumes Beer's law behavior ($A=CK+E_A$), where A is the absorbance spectra, C is a matrix of concentrations, K is the pure component spectra and $E_A$ are the spectral residuals (anything unmodelled by linear combination of C and K). Red blood cell spectra obtained using a measurement apparatus as described herein can be converted to absorbance by taking the minus Log10 of the ratio of the red blood cell spectra to a close-in-time instrumental background spectrum. Since CLS tries to minimize $E_A$, all sources of spectral variation need to be modelled through the concentrations (C) and the pure component spectra (K) in order to produce accurate resultant estimates. The pure component spectrum (K) of an analyte of interest is usually already known; therefore augmentation usually occurs in the prediction process (solving for C). To prevent aberrant spectral variation (spectral variation not associated with the analyte of interest) from affecting the CLS model, the model may be proactively augmented with spectral component(s) associated with these aberrations, so that better concentration estimates of the analyte of interest can be obtained. The augmentation process may be applied during the calibration process, in order to get an accurate estimate of the spectral pure component associated with blood pressure.

At step 2202, a concentration matrix C is created to obtain the pure spectral component of blood pressure. This concentration matrix can be composed of blood pressure reference measurements ($C_{BP}$), concentrations associated spectral variance during the measurement of the red blood cell samples but not associated with the red blood cells ($C_S$), and concentrations associated with spectral variance of the instrument ($C_I$). Concentrations $C_{BP}$, $C_S$, and $C_I$ can be combined into one concentration matrix C, and used to estimate the pure spectral components that can be used for later predictions.

At step 2204, the blood pressure reference values ($C_{BP}$) are obtained. The blood pressure reference values $C_{BP}$ may comprise the mean of the blood pressures acquired over a period of time from a subject, to ensure the best estimate of the actual sustained blood pressures from the subject.

At step 2206, the concentrations associated with spectral variance during the measurement of the red blood cell samples ($C_S$) are obtained.

At step 2208, previously obtained pure spectral components ($K_S$) are applied. Spectral components $K_S$ may comprise spectral components of water, red blood cells, and spectral variation associated with a process applied to the red blood cells, such as drying.

At step 2210, the concentrations $C_S$ are estimated using CLS, from the pseudo inverse of the previously obtained pure spectral components $K_S$ and the absorbance spectra A. The pseudo inverse $K^+$ of the spectral components $K_S$ can be obtained using the equation $K^+=\hat{K}^T_s(\hat{K}_s\hat{K}^T_s)^{-1}$, where $\hat{K}^T_s$ is the transpose of the matrix $\hat{K}_s$.

At step 2212, the concentrations associated with the instrument variation ($C_I$) are obtained.

At step 2214, instrumental background spectra (Bkg) are applied. Background spectra Bkg may be taken during the entire period of absorbance spectra (A) data collection. These background spectra can comprise measurements of air (no sample in sample compartment of instrument), or measurements of a sample that most spectrally resembles the sample of interest, but is not the actual sample of interest (e.g., water or saline). These background spectra can be decomposed into spectral factors or components ($K_I$) by using Principal Component Analysis (PCA). The number of these spectral components ($K_I$) can be varied, such that only the largest sources of spectral variance are explained by these spectral components ($K_I$).

At step 2216, the concentrations associated with the instrument variation $C_I$ are estimated using CLS, from the pseudo inverse of the instrument variation spectral components $K_I$ and the absorbance spectra A. The pseudo inverse $K^+$ of the spectral components $K_I$ can be obtained using the equation $K^+=\hat{K}^T_I(\hat{K}_I\hat{K}^T_I)^{-1}$, where $\hat{K}^T_I$ is the transpose the matrix $\hat{K}_I$.

At step 2218, the calibration model is built by using a CLS calculation to obtain the pure component spectra K of which the component of interest resides, from the pseudo inverse of the concentration matrix C and absorbance spectra. The pseudo inverse $C^+$ of the concentrations C can be obtained using the equation $\hat{K}=(C^TC)^{-1}C^T$, where $C^T$ is the transpose the matrix C. The spectral component of interest can be, for example, the component associated with blood pressure.

At step 2220, the concentration C of the component of interest is predicted using traditional CLS, from the pseudo inverse of the pure component spectra K and the absorbance spectra A. The pseudo inverse $K^+$ of the spectral components K can be obtained using the equation $K^+=\hat{K}^T(\hat{K}\hat{K}^T)^{-1}$, where $\hat{K}^T$ is the transpose of the matrix $\hat{K}$. The concentration C can be, for example, the blood pressure level. Using this prediction model, blood pressure may be predicted using spectral data of blood samples acquired in the future by using traditional or augmented CLS methods.

The method 2200 discloses a method of predicting blood pressure from spectroscopic data from blood samples, in accordance with embodiments. A person of ordinary skill in the art will recognize many variations and modifications based on the disclosure provided herein. For example, some steps may be modified, some steps may be added or removed, some of the steps may comprise sub-steps, and many of the steps can be repeated.

The processor as described herein can be programmed with one or more instructions to perform one or more of the steps of the method 2200 of predicting blood pressure using blood spectroscopic measurements. Therefore, the above steps are provided as an example of a method of measuring blood pressure of the subject in accordance with embodiments.

Work in relation to embodiments suggests that the methods and apparatus disclosed herein are well suited to determine early stages of malaria, for example before a ring structure becomes visible under a microscopic view of a blood sample. As malaria can induce changes to the red blood cell membrane, the spectroscopic analysis of the red blood cell membrane as described herein can be used to identify malaria.

The spectrometer as described herein may comprise a hand held portable spectrometer for example. The spectrometer may comprise an optical window that can be wiped off subsequent to measurement of the blood sample, and used repeatedly with cleaning, for example. Alternatively, the spectrometer may comprise a consumable single use window component as described herein, for example.

Experimental

Based on the teachings disclosed herein, a person of ordinary skill in the art can identify biomarkers in blood in order to determine the presence of hypertension. A person of ordinary skill in the art can conduct experiments to identify one or more additional biomarkers in order to predict current and/or recent central aortic vessel pressures.

The apparatus can be constructed as described herein to measure the one or more biomarkers of the blood sample. A population of subjects can be measured with the apparatus to determine the presence of biomarkers and this data can be compared with measured blood pressure of the subjects. The relationship among the one or more biomarkers and blood pressure can be determined with one or more analytic models as described herein. For example, the high blood pressure of the subject can be identified in response to the amount of biomarker measured, and the high blood pressure can be presented to the physician as one or more of an index or a scale. In many embodiments, the amount of biomarker can be mapped to a traditional systolic blood pressure with a mapping function such as a look up table or scaling factor. For example, the systolic blood pressure can be determined with a linear function such as

BLOOD PRESSURE=A*[CONCENTRATION OF BIOMARKER]+B where the BLOOD PRESSURE is the determined blood pressure in mm Hg in response to the CONCENTRATION OF BIOMARKER in ng/ml times the scaling constant A plus the offset constant B. The parameters A and B can be determined based on the study population, for example.

FIG. 13 shows a commercially available spectroscopy apparatus 1300 suitable for combination in accordance with embodiments. The commercially available spectroscopy apparatus may comprise an ALPHA-P spectrometer, and may comprise an evanescent wave FT-IR spectrometer for example. The commercially available evanescent wave spectrometer can be used to measure one or more model substances 1310 such as chicken red blood cells, fresh, or treated with gluteraldehyde to stiffen the membrane, for example.

Figure 14:
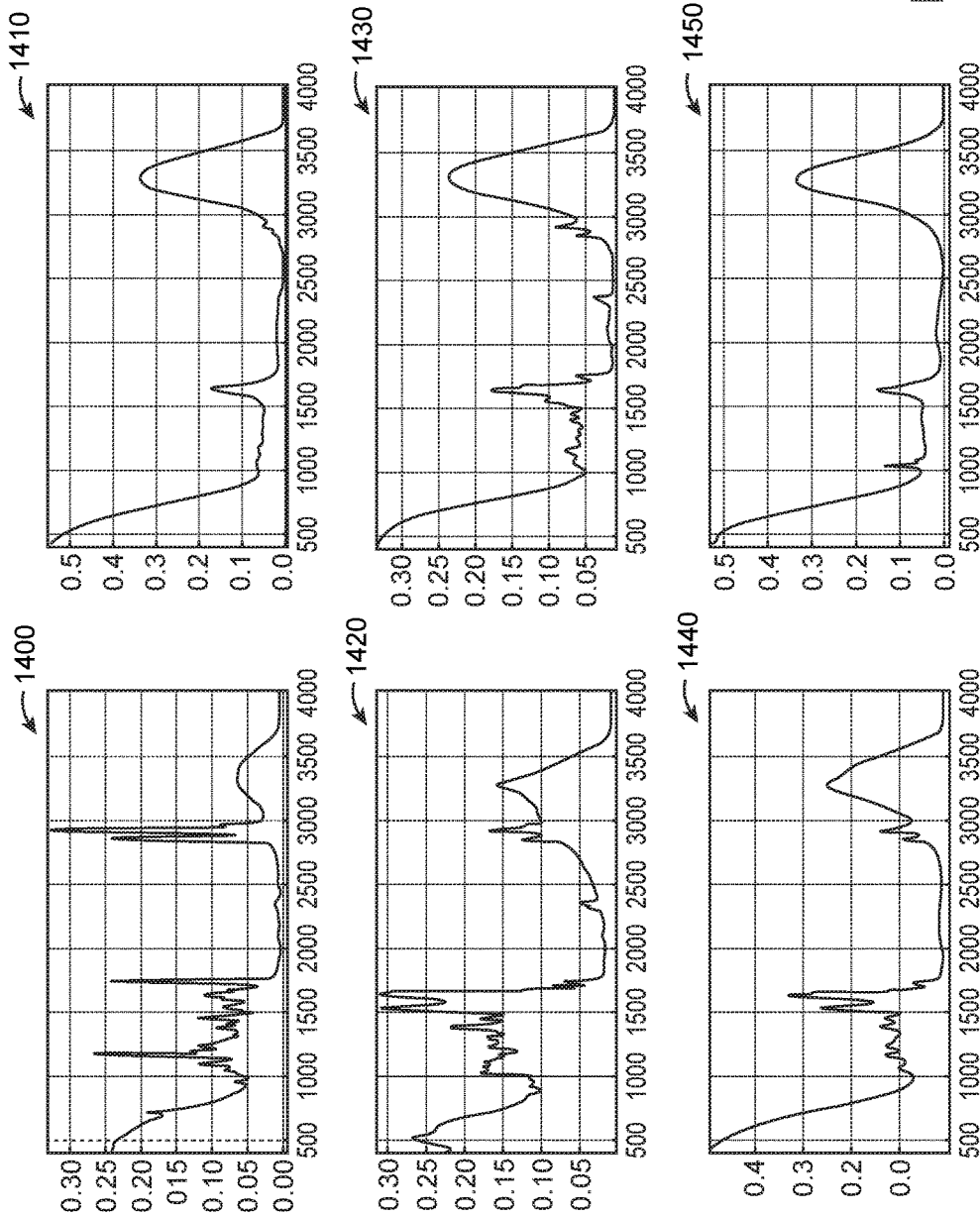
FIG. 14 shows example spectra of fat, milk, dried red blood cells, red blood cells, red meat and red wine, in accordance with embodiments.

FIG. 14 shows example spectra of fat 1400, milk 1410, dried red blood cells 1420, red blood cells 1430, red meat 1440, and red wine 1450.

Figure 15:
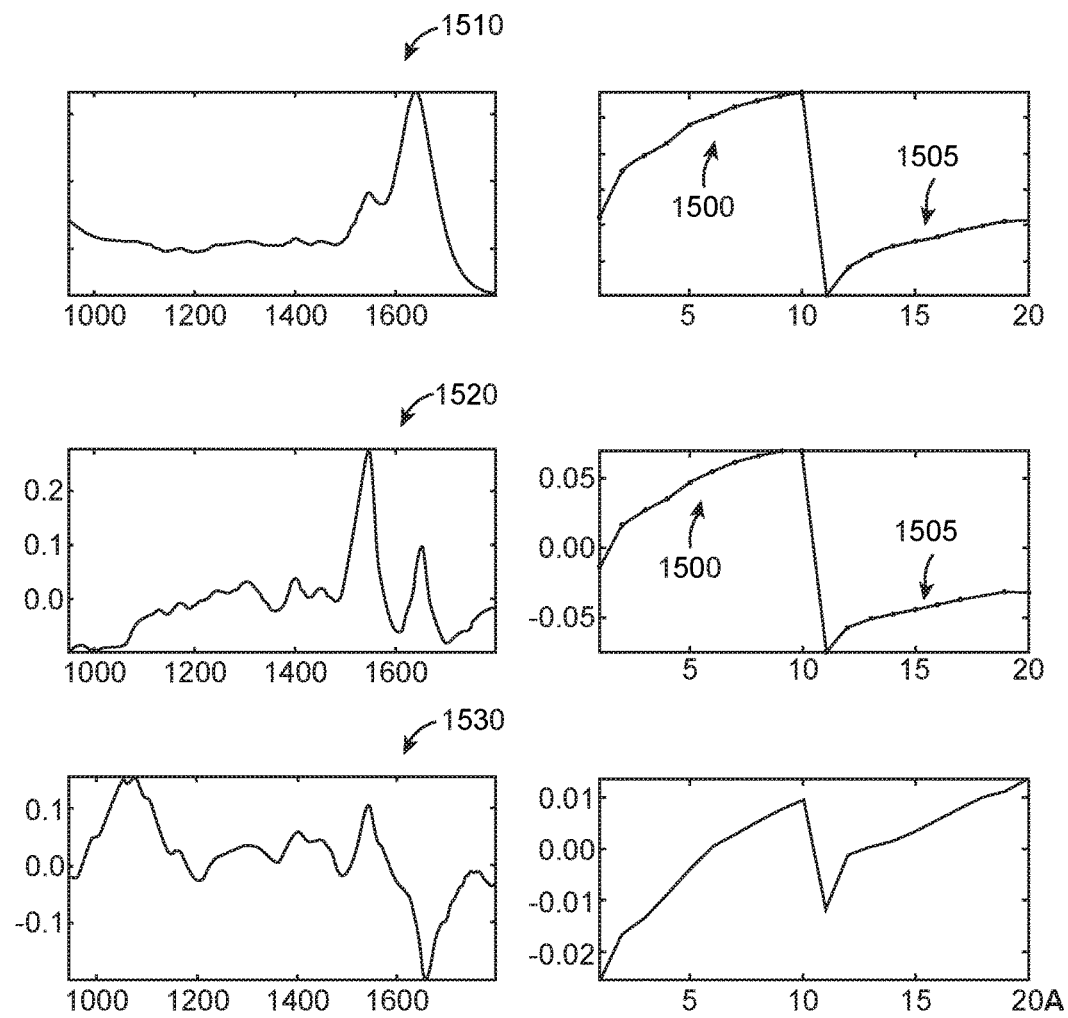
FIG. 15 shows PCA analysis of blood samples with and without aspirin, in accordance with embodiments.

FIG. 15 shows an aspirin study. The aspirin study shows principal component analysis components eigen vector 1 1510, eigen vector 2 1520, and eigen vector 3 1530. Aspirin study shows a human subject's response to a baby aspirin. The study used the first 10 spectra from each data set. PCA shows a difference in the blood sample without aspirin 1500 and blood sample with aspirin 1505. The first factor 1510 corresponds to intensity differences in the signal. The second factor 1520 corresponds to a change because of the shift in the Amide II peak (positive for the no aspirin samples and negative for the aspirin samples).

Figure 16A:
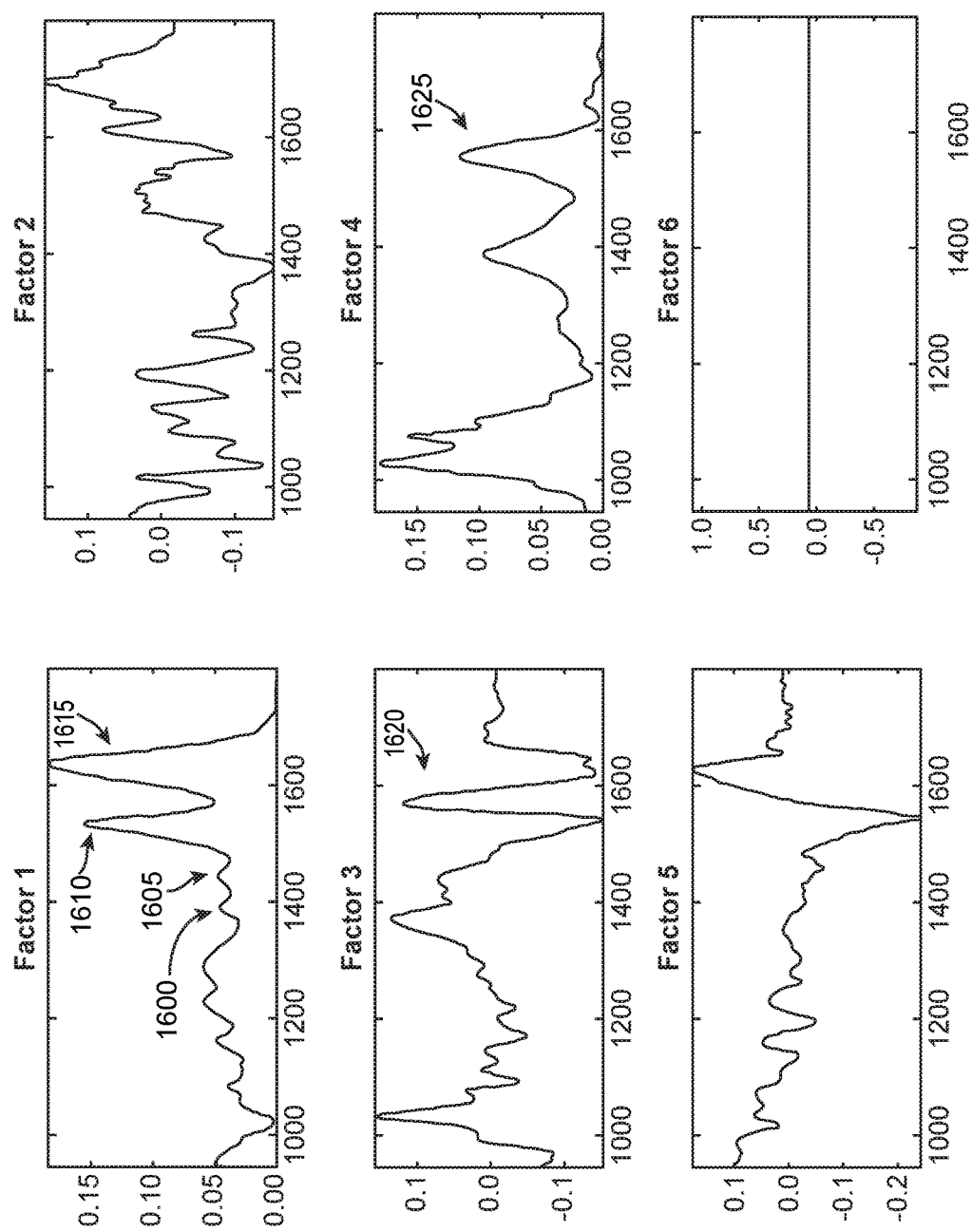
FIG. 16A shows multivariate curve resolution (MCR) factors of an aspirin study, in accordance with embodiments.

FIG. 16A shows multivariate curve resolution (MCR) factors. Factor 1 may comprise spectral peaks such as one or more of a carboxylate peak 1600, a CH3 bending peak 1605, an Amide II peak 1610, or an Amide I peak 1615, for example. Factor 3 may comprise Amide I, Amide II broadening 1620, for example. Factor 4 may comprise a water peak 1625, for example, at 1560 cm$^{-1}$ (inverse centimeters). Factor 5 may comprise a 1560 cm$^{-1}$ shift. Factor 6 may comprise a baseline offset, for example. Many additional factors can be used in accordance with the embodiments described herein, for example.

Figure 16B:
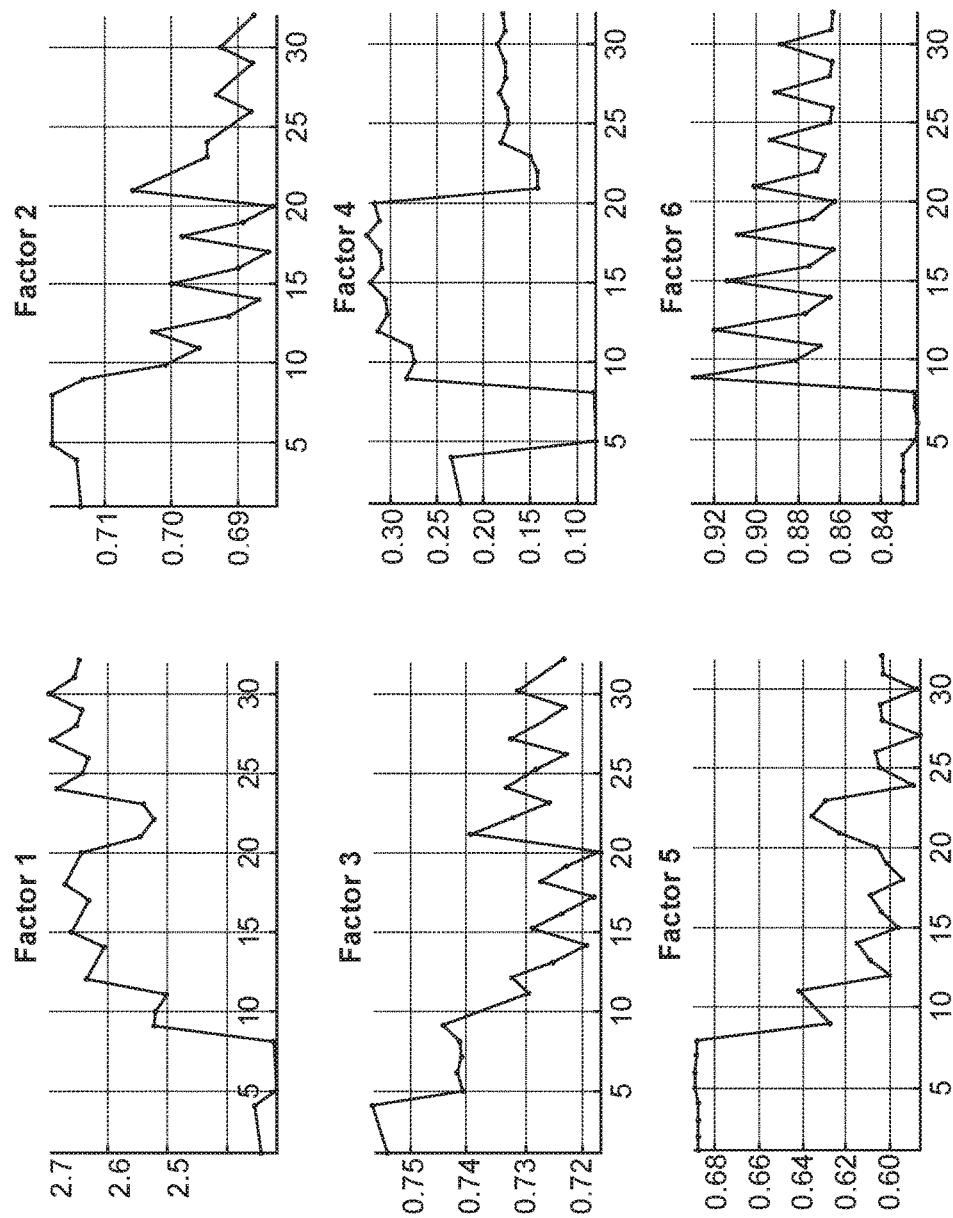
FIG. 16B shows MCR concentrations for the factors of FIG. 16A, in accordance with embodiments.

FIG. 16B shows MCR concentrations for the factors of FIG. 16A for chicken blood preliminary results as follows:
 1-5: Fresh Supernatant
 6-10: Gluteraldehyde Supernatant
 9-20: Fresh Cells, 3 replicates at each settling time (time 0: F1,F3,F5; time 1: F1,F3,F5; time 2: F1,F3,F5; time 3: F1,F3,F5)
 21-32: Glut Cells, 3 replicates at each settling time (time 0: G2,G4,G6; time 1: G2,G4,G6; time 2: G2,G4,G6; time 3: G2,G4,G6)

These preliminary data show concentration differences among the samples in accordance with embodiments described herein.

The analysis may comprise one or more analysis tools of commercially available software such Chemometrics metrics software available from Eigen Vector Research Incorporated, for example as listed on with World Wide Web (www.eigenvector.com/software/solo.htm). The software may comprise one or more of the following capabilities:
 Data Exploration and Pattern Recognition (Principal Components Analysis (PCA), Parallel Factor Analysis (PARAFAC), Multiway PCA)
 Classification (soft independent modeling of class analogies (SIMCA), k-nearest neighbors, Partial Least Squares (PLS) Discriminant Analysis, Support Vector Machine Classification, Clustering (Hierarchical Cluster Analysis, HCA))
 Linear and Non-Linear Regression (PLS, Principal Components Regression (PCR), Multiple Linear Regression (MLR), Classical Least Squares (CLS), Support Vector Machine Regression, N-way PLS, Locally Weighted Regression)
 Self-modeling Curve Resolution, Pure Variable Methods (Multivariate Curve Resolution (MCR), Purity (compare to SIMPLSMA), CODA_DW, CompareLCMS)
 Curve fitting and Distribution fitting and analysis tools
 Instrument Standardization (Piece-wise Direct, Windowed Piece-wise, OSC, Generalized Least Squares Preprocessing)
 Advanced Graphical Data Set Editing and Visualization Tools
 Advanced Customizable Order-Specific Preprocessing (Centering, Scaling, Smoothing, Derivatizing, Transformations, Baselining)
 Missing Data Support (Singular Value Decomposition (SVD) and Non-Linear Iterative Partial Least Squares (NIPALS))
 Variable Selection (Genetic algorithms, Iterative PLS (IPLS), Selectivity, Variable Importance Projection (VIP))

Figure 17:
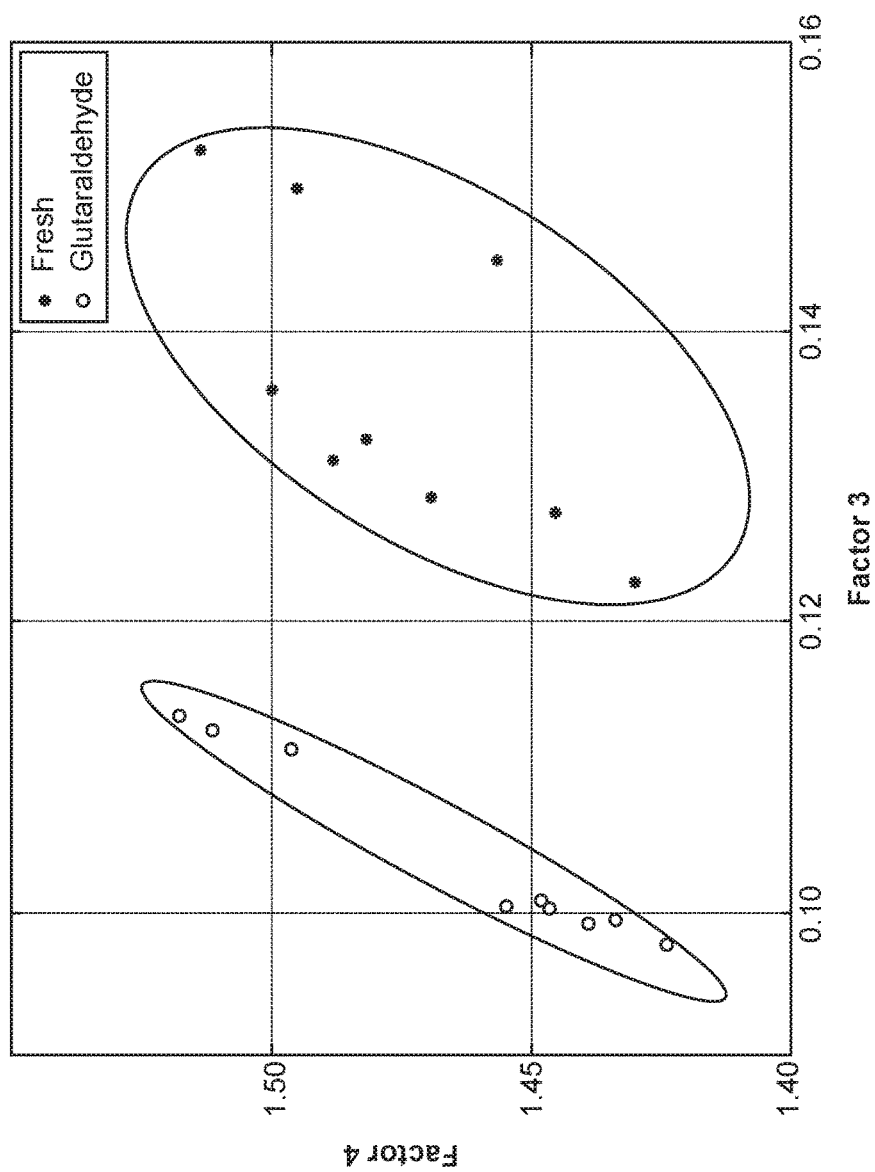
FIG. 17 shows a comparison between fresh and gluteraldehyde-stiffened chicken red blood cells (measurement time of one minute), in accordance with embodiments.

FIG. 17 shows results from a study with gluteraldehyde-treated red blood cells. A scatter plot of MCR Factor 3 in relation to Factor 4 is shown. The data are shown for combined settling times of 2, 4, and 6 minutes. Membrane secondary structural changes can be induced by brief treatment with gluteraldehyde. Washed intact chicken red blood cells were obtained, some fresh and some treated briefly with gluteraldehyde. Membrane secondary structural changes are clearly visible based on the comparison of Factor 3 and Factor 4.

Gluteraldehyde induces structural changes in the red blood cell membrane and is capable of denaturing proteins. Without being bound by any particular theory, the spectral changes induced by gluteraldehyde can have at least some similarity to spectral changes induced by blood pressure of the subject. For example, the red blood cell of the hypertensive subject can be more deformable than a subject having normal blood pressure. Gluteraldehyde is a cross-linking molecule that affects the structural rigidity of the red blood cell membrane.

Figure 18:
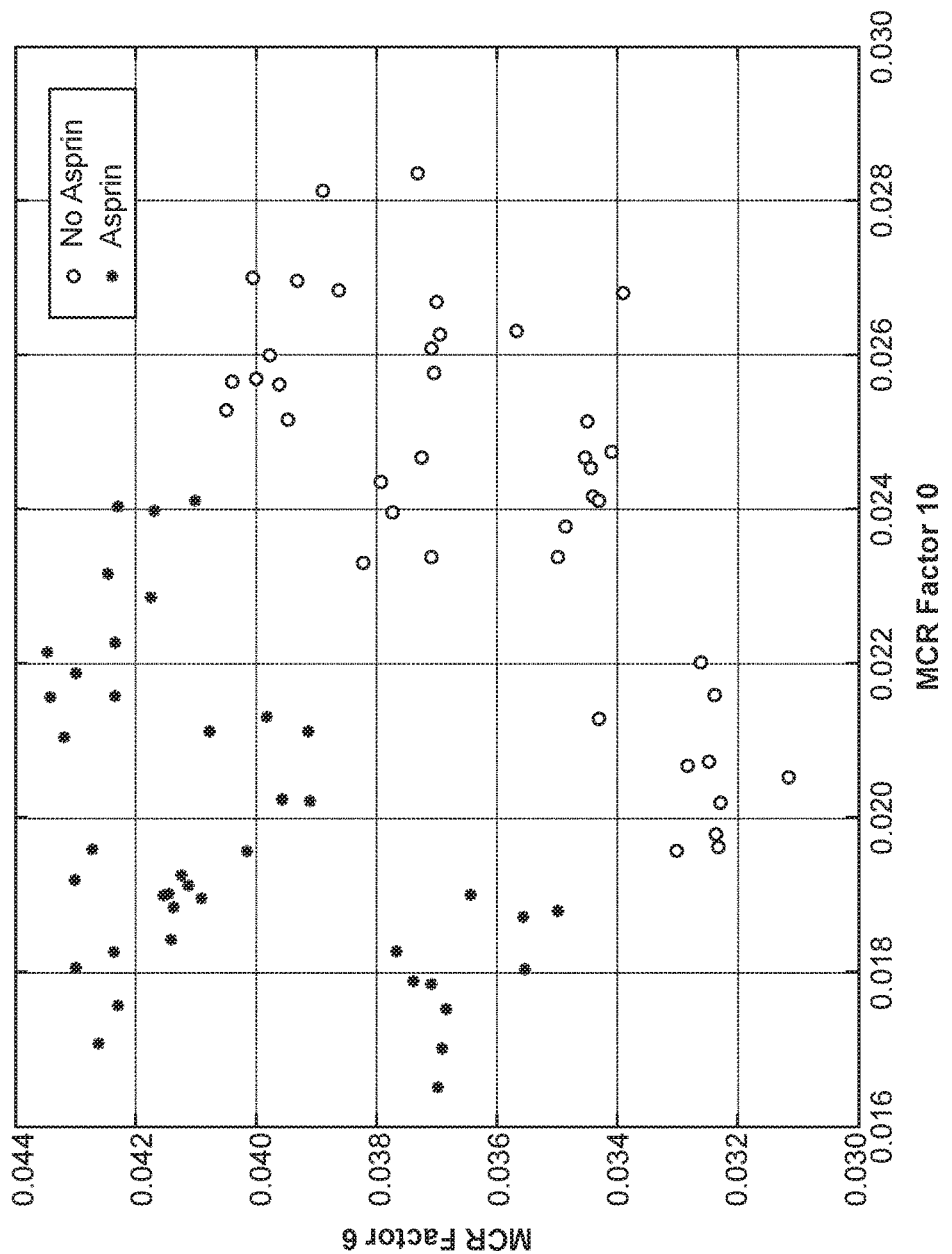
FIG. 18 shows the effect of aspirin on the red blood cell membrane, in accordance with embodiments.

FIG. 18 shows results from a study with human blood and aspirin. Whole blood from one volunteer was obtained via fingerstick before and after the ingestion of acetylsalicylic acid (ASA, aspirin). Aspirin induces membrane structural changes in the red blood cell. A drop of heparinized blood was measured directly on a horizontal sampler and spectra were acquired while allowing the red blood cells to gravimetrically separate from whole blood and deposit onto the sampler window. This was done to allow chemometric separation of the pure membrane spectrum. Data were analyzed using multivariate curve resolution (MCR). This experiment was repeated 4 times on 4 separate days, and the data set consists of 80 full infrared spectra. The data for MCR factor 6 and factor 10 show a clear separation between red blood cell membrane before and after ingestion of aspirin. Results are consistent across all 4 study days.

Figure 19:
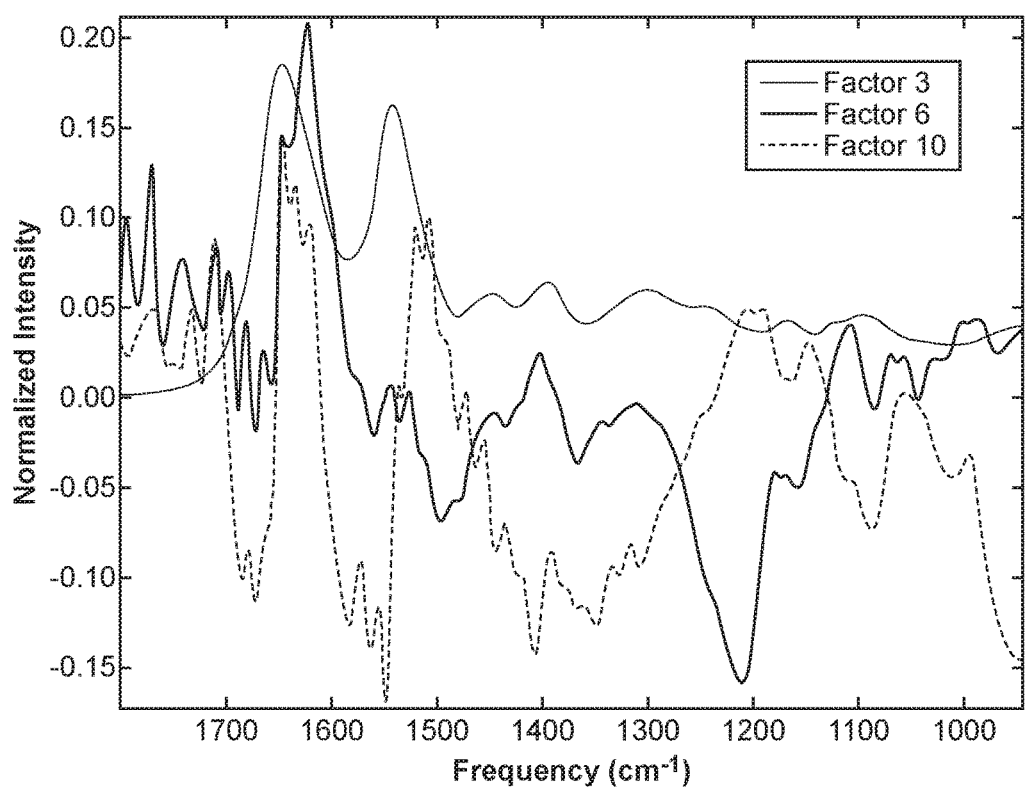
FIG. 19 shows shifts in factor 3, factor 6, and factor 10, in accordance with embodiments.

FIG. 19 shows MCR factors 3, 6, and 10, in accordance with embodiments. Factor 3 may correspond to the protein structure of blood. Factor 3 can be used as a reference for two or more factors that allow discrimination of blood after an oral dose of aspirin. Factor 6 may correspond to a shift in the Amide I peak. Factor 10 may correspond to a shift in Amide II, for example.

Figure 20:
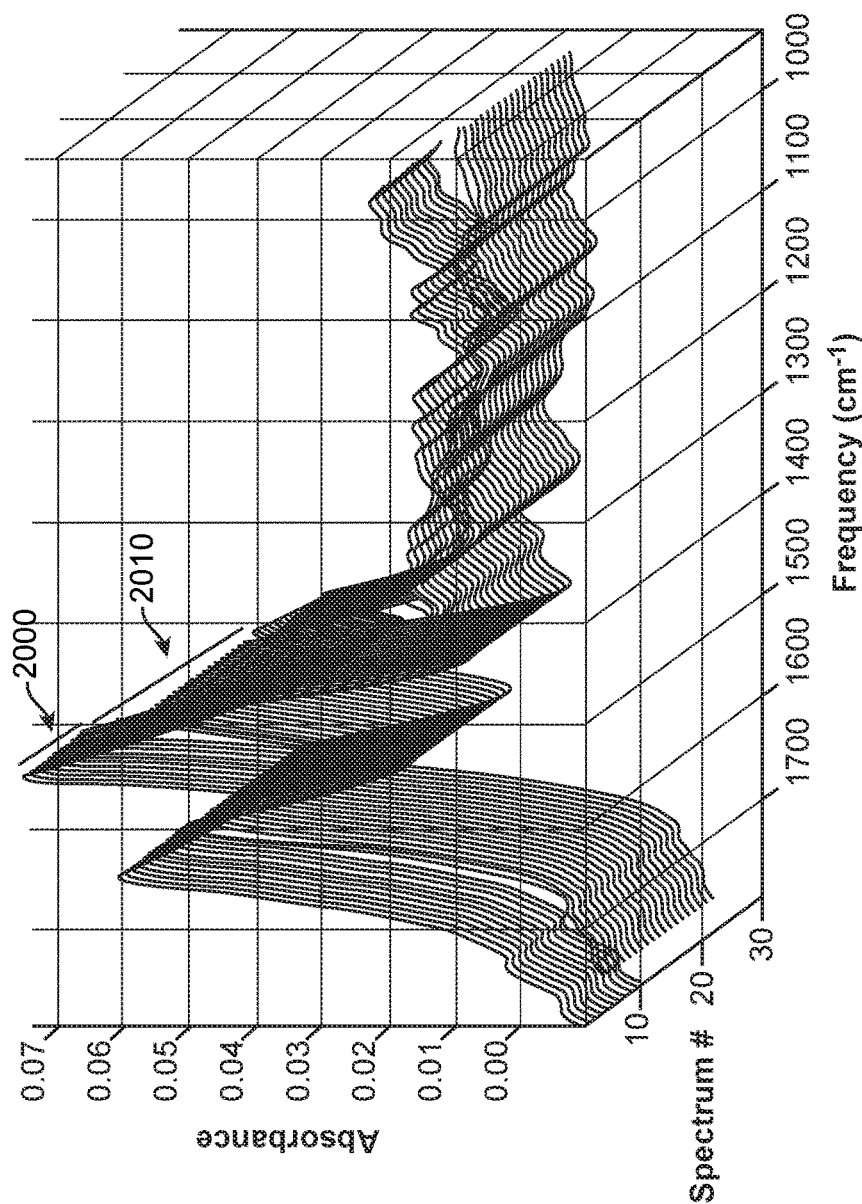
FIG. 20 shows a 3D plot of spectral data normalized to the Amide I peak for blood before and after gluteraldehyde addition, in accordance with embodiments.

FIG. 20 shows a 3D plot of results from a study of the effect of gluteraldehyde on blood.

Figure 21:
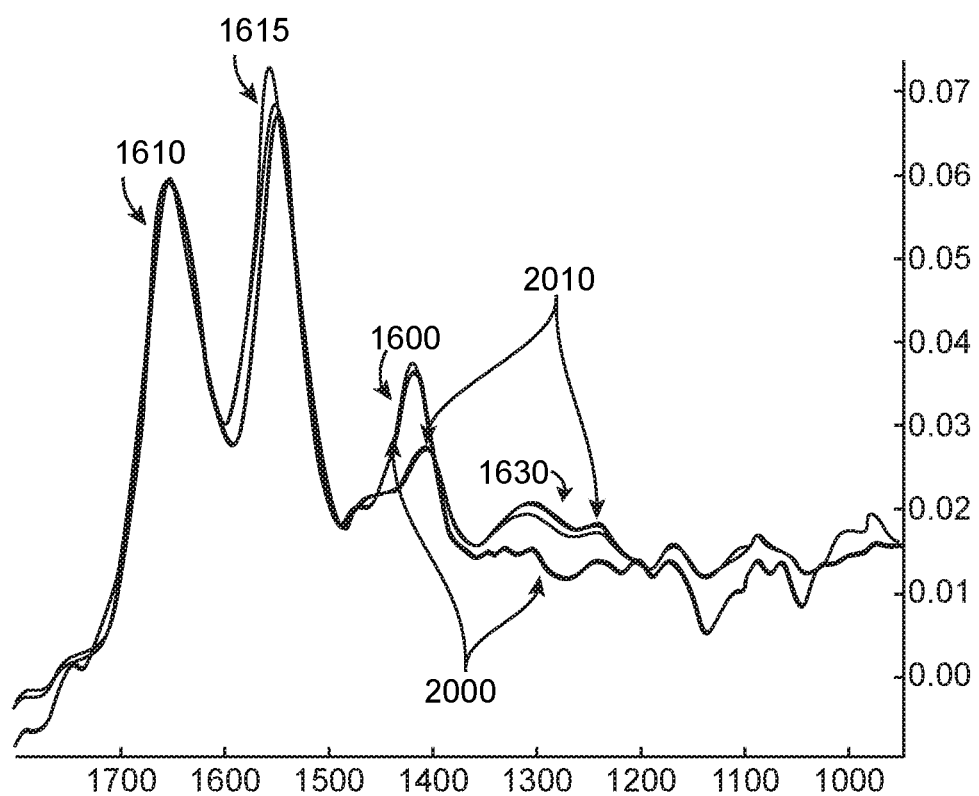
FIG. 21 shows a 2D plot of the spectral data of FIG. 20.

FIG. 21 shows a 2D plot of the data of FIG. 20. Factor 3 represents the protein structure of the blood and is used as a reference for factors 6 and 10. Factor 6 predominantly exhibits a shift in Amide I. Factor 10 predominantly exhibits a shift in Amide II.

Spectra were taken on an untreated blood sample and the last ten equilibrated spectra 2000 were selected for use in the further analysis. Blood was treated with gluteraldehyde and spectra were taken, with the last ten equilibrated spectra 2010 being selected for use in the further analysis. Spectral data were normalized to the Amide I peak 1610. Changes from after the gluteraldehyde treatment include a small shift in the Amide I peak, a larger shift in the Amide II peak 1615, a change in Carboxylate peak 1600 intensity, and an increase in Amide III band 1630.

Figure 23:
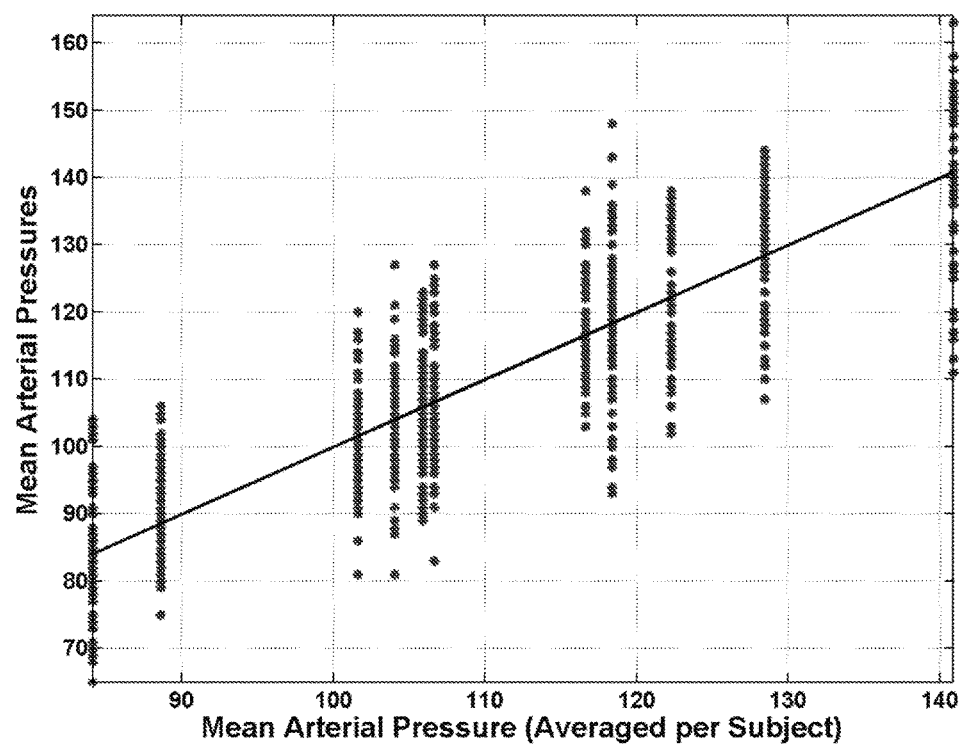
FIG. 23 shows results from a study of mean arterial blood pressure measurements in human subjects using a sphygmomanometer or blood pressure cuff.

FIG. 23 shows results from a study of mean arterial blood pressure (MAP) measurements in human subjects using a sphygmomanometer or blood pressure cuff. Blood pressure was monitored in 11 subjects, 8 having high blood pressure (systolic 140-170 mmHg/diastolic 90-120 mmHg) and 3 having normal to low blood pressure, over a period of 28 days. Subjects were trained in the use of an ambulatory blood pressure (ABP) monitoring device (Welch Allyn ABPM6100 Blood Pressure Monitor), designed for 24-hour blood pressure monitoring. Subjects recorded blood pressure readings once every day for 5 days of a week, and 6 times a day for 2 days of a week. FIG. 23 shows the MAP values (mmHg) averaged per subject, wherein the MAP values were calculated from the systolic (SP) and diastolic (DP) cuff measurements using the equation MAP=((2×DP)+SP)/3. In FIG. 23, each vertical "line" of data points represents MAP measurements for a single subject, and the sloped line going through all of the vertical "lines" of data points shows the average of the MAP measurements for each subject over the 28-day study period. The data shows the wide variation in the cuff measurements for each subject over the study period. Any one of the data points in each vertical "line" of data points may represent a single cuff measurement taken from a patient, and as shown in FIG. 23, a single cuff measurement may be significantly different from the average MAP value for the patient over the 28-day study period (data point through which the sloped line extends). It is generally recognized that the average level of blood pressure over prolonged periods of time represents the measure of blood pressure that is most clearly related to morbid events in patients. However, clinic measurement often comprise single cuff readings taken in the office, and ambulatory blood pressure (ABP) monitoring are not widely used because the devices may be cumbersome and inconvenient for patients. The results of the study in FIG. 23 show that single cuff readings can often be inaccurate in determining the patient's true average blood pressure over a prolonged period of time.

Figure 24:
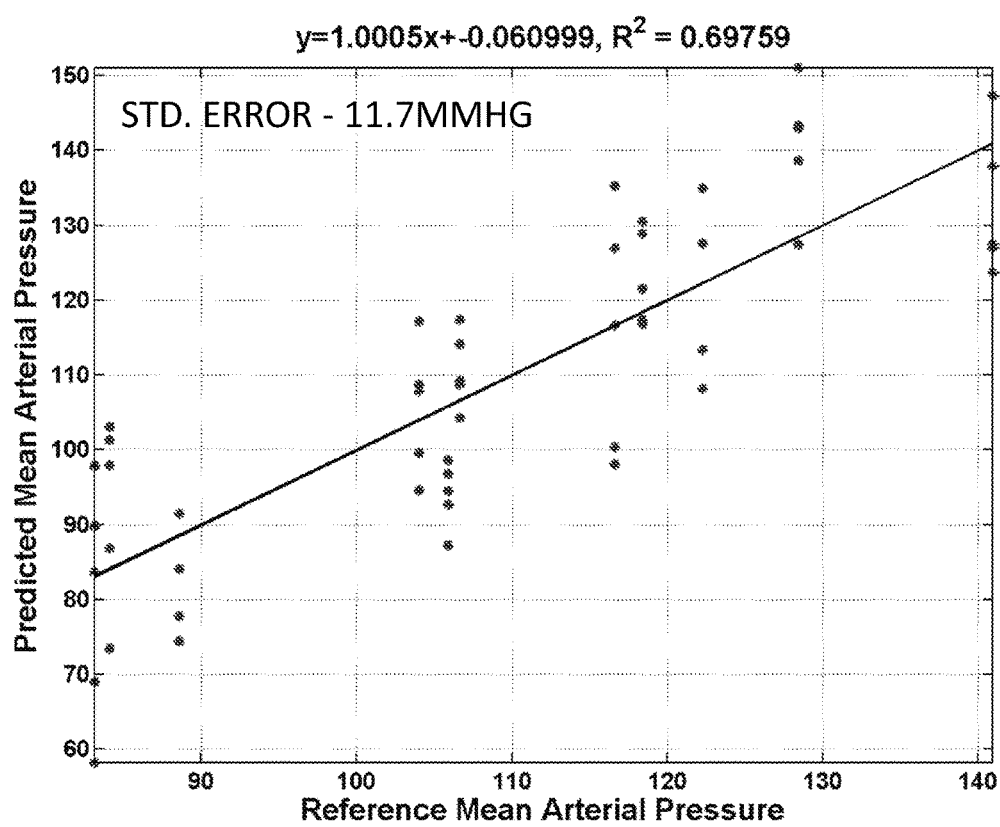
FIG. 24 shows results from a study of mean arterial blood pressure measurements in human subjects using a measurement apparatus in accordance with embodiments.

FIG. 24 shows results from a study of mean blood pressure measurements in human subjects using a measurement apparatus in accordance with embodiments. Blood samples were drawn once a day over the 28-day study period from the same 11 subjects as in the study of FIG. 23. The blood samples were analyzed using the measurement apparatus as described herein, using TIR spectroscopy to measure changes in the membrane of the red blood cells in the blood samples. Subsequently, spectroscopic data was analyzed using Augmented Classical Least Squares methods as described herein. The analyzed spectroscopic data was converted to predicted blood pressure values (mmHg) using a prediction function as described herein. FIG. 24 shows the predicted mean arterial pressure (MAP) values (mmHg) derived from spectroscopic measurements of blood samples for each subject over the 28-day study period, such that each vertical "line" of data points represents predicted MAP values from blood measurements from a single subject. The predicted MAP values are graphed against reference MAP measurements, derived from cuff measurements as described for FIG. 23, and the sloped line going through the data points shows the average of the MAP measurements for each subject over the 28-day study period. FIG. 24 shows that the predicted MAP values derived from blood spectroscopic measurements are able to predict the average MAP measurements with a standard error of about 11.7 mmHg, and a coefficient of determination ($R^2$) of about 0.7. Comparing the results of FIG. 24 with the results of FIG. 23, it can be seen that a single blood spectroscopic measurement, represented by a single data point in each vertical "line" of data points, can more closely predict the average MAP value for a patient over the 28-day study period (data point through which the sloped line extends) than a single cuff reading, represented by a single data point in each vertical "line" of data points in FIG. 23. The accuracy of predicting average blood pressure values using blood spectroscopic measurements may be further improved by appropriate modifications to the measurement apparatus and/or data analysis algorithms. While FIG. 24 shows mean arterial pressure values, the spectroscopic data can be converted to systolic blood pressure, diastolic blood pressure, pulse pressure, or any other clinically relevant measure of blood pressure. It is noted that for the results of one of the subjects shown in FIG. 24, in-clinic mercury sphygmomanometer measurements were for substituted for the subject-provided ABP measurements in deriving the reference MAP measurements, because the ABP monitoring device used by the subject was found to be functioning improperly during the course of the study.

Figure 25:
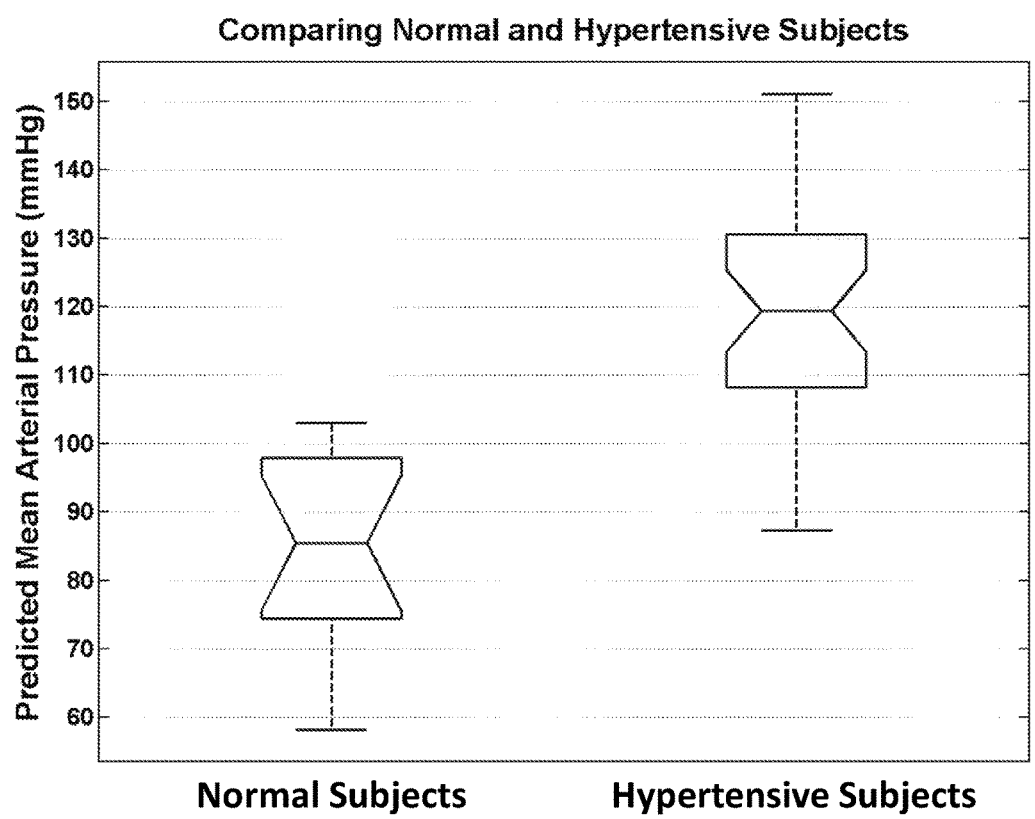
FIG. 25 shows additional results from the study of FIG. 24.

FIG. 25 shows additional results from the study of FIG. 24. The study was conducted in 11 human subjects, 8 having high blood pressure (systolic 140-170 mmHg/diastolic 90-120 mmHg; "hypertensive") and 3 having normal to low blood pressure ("normal"). The predicted mean arterial pressure (MAP) values (mmHg) derived from blood sample spectroscopic measurements were averaged per subject group ("normal" and "hypertensive"). In FIG. 25, the center line of each box plot represents the median of the MAP values for each subject group, while the top and bottom of the boxes represent $25^{th}$ and $75^{th}$ percentiles. FIG. 25 shows that for predicted MAP values obtained from blood spectroscopic measurements, the median MAP of the "normal" subject group is found to be statistically different from the "hypertensive" subject group, with 95% confidence.

Work in relation with embodiments suggests that the methods and apparatus as described herein may be well-suited for the measurement of blood samples that have been stored up to about 3 days after collection. No significant changes in spectroscopic data of blood samples were observed during such a time window, when red blood cells were purified, washed, and stored under appropriate refrigeration conditions.

Spontaneously Hypertensive Mouse and Rat Studies

Work in relation to embodiments suggests that animal models can be used to identify biomarkers suitable for use in humans. Vertebrate erythrocytes consist mainly of hemoglobin. The mammalian red blood cell comprises similar structures, proteins, and biomarkers among many species including mammals such as humans, rats, and mice. Mammalian erythrocytes typically have a biconcave disk shape, which optimizes their flow properties in larger vessels. Generally, mammalian erythrocytes are flexible and deformable to enable passage through small capillaries.

Mammalian erythrocytes are non-nucleated in their mature form, and also lack all other cellular organelles. Consequently, they lack DNA and cannot synthesize RNA. Structural properties are linked to the membrane. The membrane comprises a lipid bilayer, membrane proteins, lipids, and carbohydrates. The membrane is composed of three layers: the outer, carbohydrate-rich glycocalyx, the lipid bilayer, and the membrane skeleton. Mammalian erythrocyte lipid bilayers contain similar compositions of phospholipids, including choline phospholipids (CPs), acidic phospholipids (APs), and phosphatidylethanolamine (PE).

Spontaneously hypertensive rats, and similar model mice, comprise attributes that can be suitable for identification of blood markers of health of humans, in accordance with embodiments.

High-density lipoprotein (HDL) and low-density lipoprotein (LDL) are both present in humans, mice, and rats. Wild-type mice are usually resistant to lesion development and clear LDL very quickly. Mouse models more useful for comparison to humans have been developed. For example, low-density lipoprotein receptor-deficient mice (LDLR−/− mice) and apolipoprotein E-deficient mice (apoE−/−mice) are widely used. LDLR−/−mice respond effectively to peroxisome proliferator-activated receptor (PPAR) agonists, which are used in humans as well to reduce triglycerides (TG) and LDL cholesterol and to raise HDL cholesterol. ApoE−/−mice develop extensive atherosclerotic lesions, and respond to treatment with statins and PPAR agonists, as do humans.

The spontaneously hypertensive rat (SHR) is another animal model of primary hypertension commonly used to study cardiovascular disease. Around 5-6 weeks of age, the SHR begins hypertensive development. In adult age, systolic pressures reach 180-200 mmHg. Around 40-50 weeks, the SHR typically develops characteristics of cardiovascular disease, such as vascular and cardiac hypertrophy. Similar models have been developed in mice, such as JAX BPL/2 mice. BPL/2 mice develop elevated systolic blood pressure at five weeks of age, and by 150 days of age show an average blood pressure of 119 mmHg. This predictable progression allows longitudinal studies of the same population both before and after hypertensive development. Such studies can show biomarker levels and other changes associated with the onset of hypertension and/or the impacts of hypertension.

With the teachings of the present disclosure, a person of ordinary skill in the art can conduct experiments to measure and identify blood based biomarkers to determine the health of a human subject without undue experimentation.

Reference is made to the following claims which recite combinations that are part of the present disclosure, including combinations recited by multiple dependent claims dependent upon multiple dependent claims, which combinations will be understood by a person of ordinary skill in the art and are part of the present disclosure.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

We claim:

1. A method of identifying a change in an amount of a biomarker from blood of a subject, the method comprising:
   providing a blood sample into a capillary tube, the blood sample comprising the biomarker;
   passing a first beam of light through the capillary tube and through the blood sample at a first time;
   detecting the first beam of light to obtain a first spectral pattern comprising a spectral band of frequencies corresponding to the biomarker;
   determining, by measuring the spectral band of frequencies from the first spectral pattern, a first biomarker measurement indicating a first amount of the biomarker;
   separating the blood sample in the capillary tube by gravimetric separation into a plurality of blood components, wherein the plurality of blood components comprises the biomarker;
   passing a second beam of light through the capillary tube and through at least one of the plurality of blood components at a second time;
   detecting the second beam of light to obtain a second spectral pattern comprising the spectral band of frequencies corresponding to the biomarker;
   determining, by measuring the spectral band of frequencies from the second spectral pattern, a second biomarker measurement indicating a second amount of the biomarker; and
   determining the change in the amount of the biomarker in response to the first biomarker measurement and the second biomarker measurement by correlating changes in the blood sample as exhibited in changes between the first and second spectral patterns.

2. The method of claim 1, wherein the capillary tube is heparinized.

3. The method of claim 1, wherein the blood sample provided into the capillary tube is drawn from an external surface of a finger of the subject.

4. The method of claim 1, wherein separating the blood sample into the plurality of blood components comprises separating the blood sample into one or more of a serum component, a plasma component, a cellular component, a red blood cell component, a white blood cell component, or a platelet component.

5. The method of claim 1, further comprising pressurizing the capillary tube to pressurize the blood sample in the capillary tube.

6. The method of claim 5, further comprising pressurizing the capillary tube to a first pressure before obtaining the first biomarker measurement and pressurizing the capillary tube to a second pressure higher than the first pressure before obtaining the second biomarker measurement to cause denaturation of components of the blood sample.

7. The method of claim 6, wherein determining the change in the amount of the biomarker is further based on comparing the first and second biomarker measurements to one or more temporal denaturation profiles of the biomarker developed from prior pressurization measurements.

8. The method of claim 1, further comprising heating the blood sample in the capillary tube before one or more of the first or second biomarker measurements is obtained.

9. The method of claim 1, further comprising cooling the blood sample in the capillary tube before one or more of the first or second biomarker measurements is obtained.

10. The method of claim 1, wherein one or more of the first or second biomarker measurements is obtained with transmission spectroscopy.

11. The method of claim 1, wherein the first biomarker measurement is obtained through a first measurement channel by placing the capillary tube on a first optical measuring surface, the second biomarker measurement is obtained through a second measurement channel by placing the capillary tube on a second optical measuring surface, and the first optical measuring surface comprises a different optical measuring surface than the second optical measuring surface.

12. The method of claim 1, wherein one or more of the first or second beams of light comprises an infrared or near-infrared light beam.

13. The method of claim 1, wherein one or more of the first or second amounts of the biomarker indicates one or more of a presence, or absence of the biomarker.

14. The method of claim 1, further comprising identifying a blood component corresponding to the biomarker in response to one or more of the first or second spectral patterns.

15. The method of claim 1, wherein the second time is after the first time such that the first and second spectral patterns comprise a time series of spectra.

16. The method of claim 15, further comprising identifying a blood component corresponding to the biomarker in response to the time series of spectra.

17. The method of claim 1, wherein the biomarker corresponds to one or more of adenosine triphosphate, or, one or more transmembrane proteins, one or more proteins of a membrane skeleton, one or more lipids of a red blood cell membrane, a relative ratio of the one or more lipids of the red blood cell membrane, or biomaterial deposited on a surface of the red blood cell membrane.

18. The method of claim 1, wherein the biomarker corresponds to one or more of a protein, a lipid, a high density lipoprotein, a low density lipoprotein, membrane protein, a transmembrane protein, or a spectrin network, and wherein spectra of the biomarker comprise one or more of an Amide I peak, an Amide II peak, a Carboxylate peak, or an Amide III band.

19. The method of claim 18, further comprising:
analyzing the first and second spectral patterns to identify one or more of the Amide I peak, the Amide II peak, the Carboxylate peak, or the Amide III band; and
identifying a blood component corresponding to the biomarker in response to the analysis.

20. The method of claim 1, wherein the biomarker comprises a plaque biomarker.

21. The method of claim 20, wherein the plaque biomarker comprises a material of one or more of a foam-cell rich plaque, a lipid-rich plaque, or a collagen-rich plaque.

22. The method of claim 1, wherein the biomarker comprises a blood pressure biomarker.

* * * * *